United States Patent
Aldahlawi et al.

(10) Patent No.: US 11,285,104 B1
(45) Date of Patent: Mar. 29, 2022

(54) ORAL ADMINISTRATION OF 5-FU IN A GELLING NANOSUSPENSION FOR TARGETED DELIVERY TO TREAT COLORECTAL CANCERS

(71) Applicant: King Abdulaziz University, Jeddah (SA)

(72) Inventors: Alia M Aldahlawi, Jeddah (SA); Sahar R El Hadad, Jeddah (SA); Samaa T Abdullah, Jeddah (SA)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 0 days.

(21) Appl. No.: 17/326,826

(22) Filed: May 21, 2021

Related U.S. Application Data

(62) Division of application No. 17/071,093, filed on Oct. 15, 2020, now Pat. No. 11,058,635.

(51) Int. Cl.
| | |
|---|---|
| *A61K 9/51* | (2006.01) |
| *A61K 9/06* | (2006.01) |
| *A61K 31/513* | (2006.01) |
| *A61K 9/50* | (2006.01) |

(52) U.S. Cl.
CPC .............. *A61K 9/06* (2013.01); *A61K 9/5036* (2013.01); *A61K 9/5192* (2013.01); *A61K 31/513* (2013.01)

(58) Field of Classification Search
CPC .... A61K 9/008; A61K 9/1682; A61K 9/1605; A61K 9/286
See application file for complete search history.

(56) References Cited

U.S. PATENT DOCUMENTS

2011/0280945 A1* 11/2011 Lebon ............... A61P 3/06 424/494

FOREIGN PATENT DOCUMENTS

CN      107823177 A  *  3/2018

OTHER PUBLICATIONS

Aoyama et al (Effect of High Molecular Weight Sodium Alginate on the Viscosity and Characteristic of Alginate Impression Materials; Prosthodont Res Pract 6: 239-245, 2007) (Year: 2007).*

* cited by examiner

*Primary Examiner* — Micah Paul Young
(74) *Attorney, Agent, or Firm* — WC&F IP

(57) ABSTRACT

A sustained-release formulation of 5-fluorouracil (5-FU) providing a polymeric coating in a nanosuspension comprising sodium alginate and carrageenan for oral administration. The nanosuspension forms an insoluble sedimenting gel in the low pH environment of the stomach to speed gastric emptying. The sedimented insoluble gel becomes soluble in the pH environment of the small intestine and is transported to the colon where 5-FU is released at a predictable rate. The targeted delivery to the colon inhibits loss of 5-FU in the gastrointestinal tract and increases 5-FU exposure to cancerous cells in the colon.

8 Claims, 23 Drawing Sheets

ORAL ADMINISTRATION OF 5-FU IN A GELLING NANOSUSPENSION FOR TARGETED DELIVERY TO TREAT COLORECTAL CANCERS

FIELD OF THE INVENTION

The invention generally relates to a formulation of 5-fluorouracil for oral administration as a chemotherapeutic treatment for colorectal cancer. The invention also relates to pharmaceutical compositions comprising 5-fluorouracil in a sustained-release nanosuspension for targeted delivery to the colon.

BACKGROUND

The second most lethal cancer and the third most prevalent malignant tumor is colorectal cancer (CRC), with a 5-year survival rate of 64%. Almost 10% of the newly recorded 2018 cases were reported as deaths. The most widely used CRC chemotherapeutic regimens comprise single-agents such as 5-fluorouracil (5-FU) or multiple agent regimens, which typically include various combinations of 5-FU, oxaliplatin (OX), irinotecan (IRI), and capecitabine (CAP). According to studies, the first-line single-agent therapy is not inferior to multiple agent regimens for overall survival. Patients in the early stages are recommended to take single-agent therapy. See, for example, Xie et al. *Signal Transduct Target Ther.* 5(1):22. The most widely used single agent, 5-FU, is an anti-metabolite prescribed to manage stomach, colon, lung, and breast cancer (Takiguchi et al. 2001. *Cancer Chemother Pharmacol.* 47(1):11-14.). The daily 5-FU dose is 20 mg/Kg*m$^{-2}$ of body weight or 1200 mg/m$^2$ of body surface area, per the NCCN Guidelines-2019® found on the website of the National Comprehensive Cancer Network®. However, 5-FU single-agent regimens in the colorectal cancer management currently involve multiple IV administrations that can be painful and time-consuming. Furthermore, it results in systemic exposure to FU, rather than a targeted treatment of the colorectal system.

Despite the disadvantages, IV administration of 5-FU remains as the standard of care due to the erratic and unpredictable absorption of 5-FU from the gastrointestinal tract. However, the IV route is still coupled with severe systemic side effects due to the cytotoxic nature and selectivity problems associated with 5-FU and metabolites. The biological half-life of 5-FU is 10-20 minutes after IV administration. To overcome the short half-life, one of the solutions was to re-administer the drug, which unfortunately adds to the adverse effects and low patient compliance. Another source of variation is liver first-pass metabolism, such as that describes in Giunchedi et al. 2000 *AAPS Pharm Sci Tech.* 1(3):31-36. Finally, the lack of 5-FU selectivity to target cancerous cells is also a great source of adverse effects, but this problem exists with both IV and the unapproved route of oral administration.

Barriers to oral administration include rapid gastrointestinal absorption; thus, little of the 5-FU reaches the colon. After oral ingestion, maximum plasma concentration is achieved between 15 and 60 minutes (Takiguchi et al., supra). Another problem is the gastric metabolism of 5-FU that converts it to polar metabolites. The formation of these metabolites is further complicated by the gastric emptying rate, which decreases the absorption rate, thus providing additional sources of uncertainty regarding the effective dose. These parameters also introduce yet another problem, which is variability between individuals that makes it difficult to predict the dosage needed to achieve optimal treatment.

Potential carriers of 5-FU have been tested, including polymers such as poly acrylamide-poly methacrylamide combined with poly N-isopropyl acrylamide-NA hydrogel systems (Manjula et al. 2013 *Advances in Polymer Technology.* 32(2)), polyvinyl alcohol/NA hydrogels with surface treatment (Dalei et al. 2020 *ChemistrySelect.* 5(7):2168-2178), hydroxypropyl methylcellulose with NA (Shishu et al. 2007 AAPS PharmSciTech. 8(2):E143-E149), calcium alginate (Arica et al., International Journal of Pharmaceutics. 242(1):267-269 2002, Patel et al. 2008 *Asian Journal of Pharmaceutics.* 5:24-245), pH-sensitive alginate, chitosan and $CRG_k$ dual-layered system (Sun et al. 2019 *International Journal of Biological Macromolecules.* 132:487-494), poly lactide-co-glycolide (McCarron et al. 2000 *Journal of Pharmacy and Pharmacology.* 52(12):1451-1459) or pure NA beads cross-linked with 5-FU (Olukman et al. 2012 *Journal of Biomaterials and Nanobiotechnology.* 03(04): 469-479). Many of these were tested for the ability to provide sustained release of 5-FU or for treatments of other cancers, but there is still a need for improvement.

The challenges of IV and oral administration of 5-FU highlight the need for the development of an oral formulation to enhance chemotherapy adherence and compliance. An oral delivery would be more convenient and less painful than conventional IV administration but needs to overcome the barriers and complications associated with oral formulations. Thus, there is a need for a formulation for oral administration that targets the cancerous cells or tumor(s), minimizes exposure to healthy tissues and cells, and reduces side effects.

SUMMARY OF THE INVENTION

One aspect of the invention is a pharmaceutical composition comprising a delayed-release of 5-FU in an in-situ gelling nanosuspension and methods of making and administering it as a chemotherapeutic treatment for colorectal cancer. The invention provides a targeted delivery method through the digestive tract that reduces the systemic effects of IV administration of 5-FU. The pharmaceutical formulation of the invention also increases the amount of 5-FU that reaches the colon compared to conventional formulations of 5-FU for oral administration.

In one embodiment, the invention in a pharmaceutical composition is a gelling nanosuspension that provides sustained-release of 5-FU. The formulation comprises carrageenan-coated 5-FU (CRG-FU) particles suspended in a solution of high molecular weight sodium alginate (NA). A hydrodynamic NA coating forms on the CRG-FU particles (NAH-CRG-FU) and becomes an insoluble gel at a very low pH, typically between pH1 and pH3. The insoluble gel further forms a sediment in the low pH environment to enhance the formulation's gastric emptying. The insolubility and sedimentation are reversible so that as the pH increases, thus the insoluble sedimented gel becomes soluble again. In one embodiment of the invention, NA's solution comprises a high molecular weight grade of 595,000-600,000 g/mole having a viscosity of 638 to 640 mPa in 1% water. The CRG-FU particles have a diameter of 225-250 µm when they are placed in the solution of NA.

In another embodiment, the invention is a method of formulating a pharmaceutical composition of 5-FU in a gelling nanosuspension, comprising the steps of levigating, which is described by the mixing of CRG and 5-FU in the addition of water droplets that were enough for paste formation, a mixture of carrageenan and 5-FU to produce carrageenan-coated FU (CRG-FU) particles, suspending and homogenizing the CRG-FU in a solution of high molecular weight sodium alginate (NA), and allowing a hydrodynamic NA coating to form on the CRG-FU particles (NAH-CRG-FU). The hydrodynamic NA coating becomes an insoluble gel at a pH of 3.5 or lower, and the insoluble gel reversibly becomes soluble as the pH increases to at least 6 or higher.

The insolubility and sedimentation are reversible so that as the pH increases, thus the insoluble sedimented gel becomes soluble again. In one embodiment of the invention, NA's solution comprises a high molecular weight grade of 595,000-600,000 g/mole having a viscosity of 638 to 640 mPa in 1% water. The CRG-FU particles have a diameter of 225-250 μm before they are placed in the NA solution and have a diameter of 15-20 nm after placing them in the NA solution. In one embodiment, carrageenan-kappa is used to coat the 5-FU and form CRG-FU, and excess carrageenan-lambda is added to the nanosuspension.

In one embodiment, the prepared CRG-FU particles have a diameter range of 225 to 250 μm. In another embodiment, the prepared CRG-FU particles have a diameter of less than 250 μm.

Another aspect of the invention pertains to a method of treating colorectal cancer or carcinoma in a subject in need thereof with a therapeutically effective quantity of a delayed-release formulation of 5-fluorouracil (FU) designed to target the colon. The steps of the method comprise obtaining a therapeutically effective quantity of 5-FU, coating the 5-FU with a sufficient quantity of carrageenan to produce carrageenan-coated FU (CRG-FU) particles, suspending the CRG-FU particles in sodium alginate (NA) solution wherein a hydrodynamic NA coating forms on the CRG-FU particles (NAH-CRG-FU), and administering the suspension of NAH-CRG-FU particles orally to the subject or through a nasal, esophageal or gastric tube. Examples of such tubes include a feeding tube that passes through the nasopharynx into the esophagus, a tube that enters the esophagus through an esophageal stoma, or a gastrostomy tube entering the stomach through a gastric stoma.

When the NA solution comprising NAH-CRG-FU particles encounters the pH environment contained within the stomach, the hydrodynamic NA coating forms an insoluble gel, thereby inhibiting the release of the CRG-FU. The insoluble gel further forms a sediment when at the pH environment of the stomach to get eluted. As the insoluble sedimented gel comprising NAH-CRG-FU particles moves into the small intestine where the pH is at least 6, the insoluble gel becomes soluble at a predictable rate. The release of the CRG-FU particles at the predicted rate allows the calculation of a dose that will reach the large intestine to treat colorectal cancer or carcinoma.

In one embodiment of the method of treatment, the predicted rate of release of the CRG-FU particles is calculated using the equation:

$$MDT = \frac{\sum_{i=1}^{n} t_{mid} \cdot \Delta M}{\sum_{i=1}^{n} \Delta M}$$

wherein i is the number of release samples, n is the number of release times, t is the mid-point time in the interval ($t_{i-1}-t_i$), and $\Delta M$ is the amount of FU released in the interval ($t_{i-1}-t_i$).

Depending upon the health and condition of the subject, the predictable portion of the CRG-FU particles can be administered to remain in the colon for at least 22 hours. In one embodiment of the invention, the CRG-FU particles remain in the colon for 22 to 70 hours. In another embodiment, the CRG-FU particles remain in the colon for approximately 24 hours.

In yet another embodiment, the invention is a method of preparing shelf-stable 5-fluorouracil (5-FU) nanoparticles suitable for suspension in a gelling nanosuspension for oral administration, comprising the steps of obtaining a suitable quantity of 5-FU levigating a mixture of carrageenan and 5-FU and carrageenan to produce carrageenan-coated FU (CRG-FU) particles, storing the CRG-FU particles for use within a suitable period of time, and suspending the CRG-FU particles in the gelling nanosuspension immediately prior to administering the oral dose. In one embodiment of this invention, the coating carrageenan is carrageenan-kappa. While the CRG-FU particles may have diameters within the range of 225-250 μm, in one embodiment, the particles have a diameter of 225 to 250 μm.

Other features and advantages of the present invention will be set forth in the description of invention that follows, and in part will be apparent from the description or may be learned by practice of the invention. The invention will be realized and attained by the compositions and methods particularly pointed out in the written description and claims hereof.

BRIEF DESCRIPTION OF THE DRAWINGS

The patent or application file contains at least one drawing executed in color. Copies of this patent or patent application publication with color drawings will be provided by the Office upon request and payment of the necessary fee.

The accompanying drawings, which are incorporated in and constitute a part of this specification, illustrate embodiments of the invention and, together with a general description of the invention given above, and the detailed description given below, serve to explain the invention.

DETAILED DESCRIPTION

Figure 1:
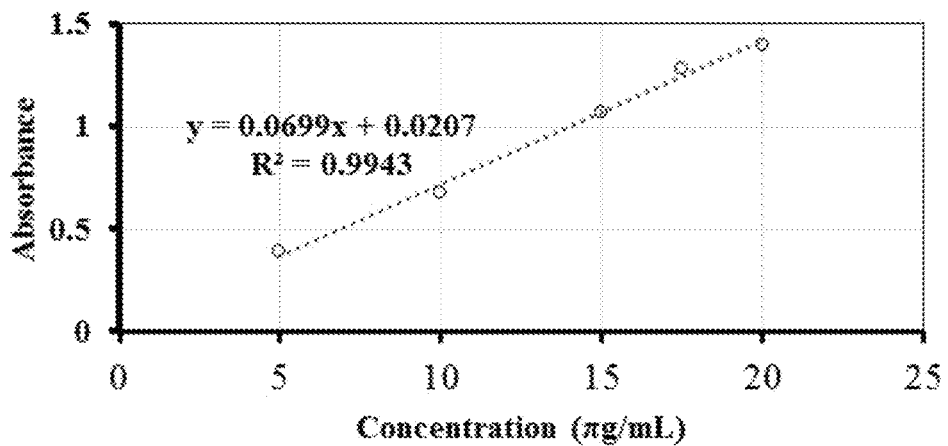
FIG. 1 shows a 5-FU calibration curve at 266 nm.

The following descriptions and examples illustrate some exemplary embodiments of the disclosed invention in detail. Those of the skill in the art will recognize that there are numerous variations and modifications of this invention that are encompassed by its scope. Accordingly, the description of a certain exemplary embodiment should not be deemed to limit the scope of the present invention.

The use of 5-fluorouracil (5-FU) as a chemotherapy agent is well-known in the treatment of colorectal cancers, but neither intravenous nor oral administration are effective at targeting the colon and cause many side effects due to off-target effects. The invention is a pharmaceutical composition comprising a delayed-release of 5-FU in a gelling nanosuspension and methods of making and administering it as a chemotherapeutic treatment for a colorectal cancer. The pharmaceutical composition is suitable for administration orally or enterally. The invention provides a method for targeted delivery through the digestive tract that reduces the systemic effects of IV administration of 5-FU. Furthermore, the pharmaceutical formulation of the invention is superior to currently available formulation for oral administration since it solves the problems associated with exposure in the stomach and thereby increases the amount of 5-FU that reaches the colon compared to conventional formulations of 5-FU for oral administration.

In one embodiment, the pharmaceutical composition is in the form of a gelling nanosuspension that provides sustained-release of 5-FU. The formulation comprises carrageenan-coated 5-FU (CRG-FU) particles, which are formed by kneading and levigating the 5-FU and carrageenan. The carrageenan may be carrageenan-kappa, carrageenan-lambda, or a combination of both. The CRG-FU composition is spread out and dried, and then the dried film is pulverized and suspended in a solution of high molecular weight sodium alginate (NA). A hydrodynamic NA coating forms on the CRG-FU particles (NAH-CRG-FU).

In addition to the NAH-CRG-FU, the nanosuspension further comprises excess NA, and excess CRG. The excess NA and CRG help to maintain the encapsulation of CRG-FU within the hydrodynamic coating and contribute to the gelling of the nanosuspension that occurs in a low pH environment. The gelling nanosuspension becomes an insoluble gel at a very low pH, typically between pH1 and pH3. The insoluble gel further forms a sediment in the low pH environment. The insolubility and sedimentation are reversible so that as the pH increases, thus the insoluble sedimented gel becomes soluble again. In one embodiment of the invention the solution of NA comprises a high molecular weight grade of 595,000-600,000 g/mole having a viscosity of 638 to 650 mPa in 1% water. The CRG-FU particles have a diameter of 225 to 250 µm when they are placed in the solution of NA. In one embodiment, carrageenan-kappa is used to coat the 5-FU and form CRG-FU, and excess carrageenan-lambda is added to the nanosuspension.

As used herein, the terms "sedimenting" and "sedimented" are used in the classical sense of the chemical property or process of sedimentation of a particle suspended in a solution. Put in other words, the gelling nanosuspension becomes an insoluble gel, and the insoluble gel is no longer suspended in the solution. The sediment is an important feature of the invention, since the sediment stimulates gastric emptying, thus shortening the residence time in the stomach. The benefit of this accrues to preservation of 5-FU as it passes through the gastrointestinal tract, thereby increasing the amount of 5-FU that reaches the colon intact.

In another embodiment. the invention is a method of formulating a pharmaceutical composition of 5-FU in a gelling nanosuspension, comprising the steps of levigating a mixture of carrageenan and 5-FU to produce carrageenan-coated FU or CRG-FU particles, suspending and homogenizing the CRG-FU in a solution of high molecular weight NA, and allowing a hydrodynamic NA coating to form on the CRG-FU particles, which are identified as NAH-CRG-FU. The hydrodynamic NA coating becomes an insoluble gel at a pH of 3.5 or lower, and the insoluble gel reversibly becomes soluble as the pH increases to at least pH 6 or higher.

The NA used in the formulation is a high molecular weight grade sodium alginate in the range of 595,000 to 600,000 g/mole and has a viscosity of 638 to 650 mPa in 1% water.

In one embodiment, the prepared CRG-FU particles have a diameter in the range of 225 to 250 µm. In another embodiment, the prepared CRG-FU particles have a diameter of less than 250 µm.

In another embodiment, the invention is a method of treating a colorectal cancer or carcinoma in a subject in need thereof with a therapeutically effective quantity of a delayed-release formulation of 5-FU designed to target the colon. The steps of the method comprise obtaining a therapeutically effective quantity of 5-FU, coating the 5-FU with a sufficient quantity of carrageenan to produce CRG-FU particles, suspending the CRG-FU particles in a NA solution wherein a hydrodynamic NA coating forms on the CRG-FU particles to produce NAH-CRG-FU in an NA solution, and administering the suspension of NAH-CRG-FU particles orally to the subject or through a nasal, esophageal or gastric tube. Examples of such tubes include a feeding tube that passes through the nasopharynx into the esophagus, a tube that enters the esophagus through an esophageal stoma, or a gastrostomy tube entering the stomach through a gastric stoma.

When the NA solution comprising NAH-CRG-FU particles encounters the pH environment contained within the stomach, the hydrodynamic NA coating forms an insoluble gel thereby inhibiting release of the CRG-FU. The insoluble gel further forms a sediment when at the pH environment of the stomach. The sediment provides an additional benefit of stimulating gastric emptying. This stimulatory effect speeds up the transit rate and decreases the amount of time that the gel remains in the stomach. As the insoluble sedimented gel comprising NAH-CRG-FU particles moves into the small intestine where the pH is at least 6, the insoluble gel becomes soluble at a predictable rate. The release of the CRG-FU particles at the predicted rate allows calculation of a dose that will reach the large intestine for treatment of the colorectal cancer or carcinoma.

While in theory there are intermediate stages of solubilization of the gel as the pH increases from the low range typically found in the stomach to the pH of the small intestine, however, it should be noted that gastric contents move from the pH of 1.2-3 of the stomach into the small intestine, where the pH is rapidly adjusted to a pH 6 or higher. Thus, while there may be a gradual solubilization that begins between pH 4.5 and pH 6, it is of little clinical relevance and thus there is no need to consider the state of the gel beyond the insolubility below pH 3.5 and increasing solubility after reaching at least pH6.

In one embodiment of the method of treatment, the predicted rate of release of the CRG-FU particles is calculated using the equation:

$$MDT = \frac{\sum_{i=1}^{n} t_{mid} \cdot \Delta M}{\sum_{i=1}^{n} \Delta M}$$

wherein i is the number of release samples, n is the number of release times, t is the mid-point time in the interval $(t_{i-1}-t_i)$, and $\Delta M$ is the amount of FU released in the interval $(t_{i-1}-t_i)$. The predicted rate of release equates to the rate of dissolution, and this rate has a direct affect on the number of daily oral doses and any adverse effects associated therewith.

Depending upon the health and condition of the subject, the predictable portion of the CRG-FU particles can be administered to remain in the colon for at least 22 hours. In one embodiment of the invention the CRG-FU particles remain in the colon for 22 to 70 hours. In another embodiment, the CRG-FU particles remain in the colon for approximately 24 hours.

In yet another embodiment, the invention is a method of preparing shelf-stable 5-FU nanoparticles suitable for suspension in a gelling nanosuspension for oral administration at a later time. Due to the nature of the gelling nanosuspension, the fully prepared nanosuspension has a relatively short half-life and it is preferred that it be administered to a patient as soon after preparation as it is reasonable to do so. However, during the course of development of the invention, the CRG-FU were found to have a longer shelf-life. Thus, the steps of preparing the CRG-FU may be performed, comprising the steps of obtaining a suitable quantity of 5-FU levigating a mixture of carrageenan and 5-FU and carrageenan to produce CRG-FU particles. The prepared CRG-FU particles may be stored for use within a suitable period of time and suspended in the gelling nanosuspension immediately prior to administering the oral dose. In one embodiment of this invention, the carrageenan is carrageenan-kappa. While the CRG-FU particles may have diameters within the range of 225 to 250 μm, in one embodiment, the particles have a diameter of less than 250 μm. The nanosuspension comprising NAH-CRG-FU is suitable for oral administration to a subject. Administration may be performed orally by swallowing the liquid, by gavage, or it may be administered via a gastrostomy, enteral feeding tube or any other suitable tube that allows delivery into the gastric lumen. While the formulation is designed to be administered orally or otherwise into the gastric lumen, it could also be administered directly into the small intestine or colon via any stoma or surgical ostomy site, thus completely bypassing the stomach.

Sodium alginate is used as the main carrying vehicle for its gelling ability. In particular, a high molecular weight grade was chosen for its ability to form an insoluble alginic acid gel in the contact with the gastric media (Hampson et al. 2010 *Drug Development and Industrial Pharmacy*. 36(5): 614-623). Carrageenans (CRG)-kappa and Lambda ($CRG_k$ and $CRG_L$) are polysaccharides isolated from the Irish moss. In order to lower the water solubility of the 5-FU, CRGs were used for coating and gelling ability that strengthens the alginic acid gel. The presence of excess CRGs in the nanosuspension enhances formation of the insoluble gel in the acid environment of the stomach.

The gastric emptying process is complex and highly variable. This makes the performance of the drug delivery system inside the body variant. This physiological problem can is solved by the invention which was designed as a drug delivery system of minimized gastric retention time. In fact, the formulation enhances gastric emptying to minimize gastric exposure and it also reduces absorption in the small intestine by encapsulating the 5-FU. In the present formulation, a one-unit liquid gastric elution system of a density more than the gastric media was designed. The faster gastric emptying or elution rate and the encapsulation and sustained release of 5-FU system were the main concepts of the present formulation. The main attempt to achieve these concepts was by drug coating and encapsulation inside an optimized mixture of pH-sensitive carrying vehicles. Additionally, 5-FU nanoparticles formulations were prepared that would add to the selectivity and efficacy of the drug (Douglas et al. 1987 *Crit Rev Ther Drug Carrier Syst*. 3(3):233-261.).

NA and CRG carrying vehicles have been used for its anti-cancer proliferative activity and considered as immunostimulant when they were used in the safe and effective dose (Mandavinia et al. 2015 *Desalination and Water Treatment*. 53(9):2529-2539, Omer et al. 2016 *International Journal of Biological Macromolecules*. 92:362-370.). In this formulation, the in-vitro drug release profile was optimized. In the optimization, the study considered the biologically effective and safe doses while the manipulation of NA and CRG amounts were conducted.

The scientific literature of the field provides a basis for the use of NA in the oral formulations for different dosage forms, purposes, release performance, physical characterizations, preparation methods and other polymers grades and compositions. Many articles discuss the use of NA as beads or multiunit solid systems, but none have provided the advantages and benefits of the present invention. Some of the previous formulations were designed to achieve a gastroretentive delivery system to treat stomach cancer (Shishu et al. 2007 *AAPS PharmSciTech*. 8(2):E143-E149). In contrast, the gelling nanosuspension of the invention aimed for colonic delivery by sedimentation of the NA gel in the presence of gastric media. In this formulation, the NA grade used was the HMWT pure NA. The formulation of the invention, with pure NA solution as a liquid vehicle and $CRG_L$ as both a coating and a carrier for 5-FU with $CRG_k$ to design the in-situ gelling and sedimenting formulation. The nanosuspension was optimized to release 5-FU as coated nanoparticles (15-20 nm in diameter) from sedimenting NA gel which has not been previously achieved.

The optimal formulation was also dependent on an optimization process for the grade of NA (low, medium and high), the CRG type for 5-FU coating (Kappa or Lambda), the CRG type used as excess liquid gel with NA (Lambda or Kappa), amounts of NA used (72, 36 or 18 mg/mL), amounts used for CRG-excess (3.5, 1.75 or 0.88 mg/mL), amounts used for CRG of the coating (4, 2, 1 or 0.75 mg/mL), the coating procedure, the stirring speed of the components and the order of addition for the components. The optimization for CRG coating (type and amount) was based on good CRG coverage of FU crystal, minimum aggregation of 5-FU, optimum 5-FU encapsulation and achieving sustained drug release of pH-profile. The optimizations for grade of NA, the CRG type used as excess liquid gel with NA, amounts of NA used, amounts used for CRG-excess, the coating procedure, the stirring speed of the components, and the order of addition for the components were based on achieving at least the minimum gastric release, sustained release profile at the intestinal-colonic phase, fast and full sedimentation of the alginic acid gel for fast gastric emptying with the maximum gel strength and durability, stable nanosuspension formation with (±40-±60 mV) zeta-potential values, the maximum loading drug loading capacity and the ability of 5-FU nanoparticles to be released as coated 5-FU to minimize the metabolism and 5-FU-free drug gastrointestinal adverse effects.

The formulation differs from others in that the 5-FU particle size achieved by with the optimum formulation of NAH-CRG-FU is lower than those previously reported by others. Additionally, the zeta-potential value of the (NAH-CRG-FU) were −40.2 mV which is the range for the stable nanoparticle. The drug release study challenged the various formulations to find the maximum release in the 300 mL media of release, total media replacement each hour, 75 rpm shaking-speed and four different pH-intervals study. Conditions found elsewhere in the scientific literature delay the drug equilibrium (sink condition) between the formulation and media to increase the release rate. Thus, use of less release volume, lower shaking-speed or less replacement volume might encourage the drug equilibrium while failing to provide a suitable formulation for oral delivery of the maximum amount of 5-FU.

Additionally, the drug encapsulation capacity for NAH-CRG-FU was 94.5±0.012%, and this has not been achieved prior to development of the present invention. It is intended to be administered orally and recommended for local treatment of cancer at intestinal-colonic area or for systemic cancer treatment. In contrast, many other formulations developed by others are suitable only for intratumor injection, IV injection or rectal administration.

The invention is intended to be a pharmaceutical composition for administration to subjects, including humans and animal subjects, particularly humans and other mammals. The terms "subject" and "patient" are used interchangeably herein, and refer to an animal such as a mammal, which is afflicted with or suspected of having, at risk of, or being pre-disposed to cancer. The terms may refer to a human. The terms also include domestic animals bred for food, sport, or as pets, including horses, cows, sheep, poultry, fish, pigs, cats, dogs, and zoo animals, goats, apes (e.g. gorilla or chimpanzee), and rodents such as rats and mice. Typical subjects include persons susceptible to, suffering from or that have suffered from cancer.

The term "treating" or "treatment", as used herein, means reversing, alleviating, inhibiting the progress of, or ameliorating the disorder or condition to which such term applies, or one or more symptoms of such disorder or condition. In particular, the invention is a method of treating a cancer, and in particular, a colorectal cancer.

The "therapeutically effective amount" is meant to be a sufficient amount of the gelling nanosuspension to provide a conventional chemotherapeutic dose. It will be understood, however, that the total daily usage of the compositions of the present disclosure will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, and rate of transit through the gastrointestinal tract; the duration of the treatment; drugs used in combination or coincidental with the gelling nanosuspension; and like factors well known in the medical arts. For example, it is well within the skill of the art to start doses at levels lower than those required to achieve the desired therapeutic effect and to gradually increase the dosage until the desired effect is achieved.

Another aspect of the disclosure relates to a pharmaceutical composition comprising a compound according to the disclosure and a pharmaceutically acceptable carrier. "Pharmaceutically" or "pharmaceutically acceptable" refer to molecular entities and compositions that do not produce an adverse, allergic or other untoward reaction when administered to a subject, such as a human, as appropriate.

In some embodiments, the compounds described herein are administered without any other active agent. In some embodiments, the compounds described herein may be combined with standard-of-care treatments (e.g., radiation therapy, hormonal therapy). In some embodiments, the compound of the disclosure may be administered sequentially or concomitantly with one or more chemotherapeutic or radiotherapeutic agents.

In one embodiment, said chemotherapeutic or radiotherapeutic agents are a therapeutic active agent used as an anticancer agent. For example, said anticancer agents include but are not limited to fludarabine, gemcitabine, capecitabine, methotrexate, mercaptopurine, thioguanine, hydroxyurea, cytarabine, cyclophosphamide, ifosfamide, nitrosoureas, platinum complexes such as cisplatin, carboplatin and oxaliplatin, mitomycin, dacarbazine, procarbazine, epipodophyllotoxins such as etoposide and teniposide, camptothecins such as irinotecan and topotecan, bleomycin, doxorubicin, idarubicin, daunorubicin, dactinomycin, plicamycin, mitoxantrone, L-asparaginase, doxorubicin, epirubicin, 5-fluorouracil and 5-fluorouracil combined with leucovorin, taxanes such as docetaxel and paclitaxel, levamisole, estramustine, nitrogen mustards, nitrosoureas such as carmustine and lomustine, *vinca* alkaloids such as vinblastine, vincristine, vindesine and vinorelbine, imatinib mesylate, hexamethylmelamine, kinase inhibitors, phosphatase inhibitors, ATPase inhibitors, tyrphostins, protease inhibitors, inhibitors herbimycin A, genistein, erbstatin, and lavendustin A. In one embodiment, additional anticancer agents may be selected from, but are not limited to, one or a combination of the following class of agents: alkylating agents, plant alkaloids, DNA topoisomerase inhibitors, antifolates, pyrimidine analogs, purine analogs, DNA antimetabolites, taxanes, podophyllotoxins, hormonal therapies, retinoids, photosensitizers or photodynamic therapies, angiogenesis inhibitors, antimitotic agents, isoprenylation inhibitors, cell cycle inhibitors, actinomycin, bleomycin, anthracyclines, MDR inhibitors and $Ca^{2+}$ ATPase inhibitors.

Additional anticancer agents may be selected from, but are not limited to, cytokines, chemokines, growth factors, growth inhibitory factors, hormones, soluble receptors, decoy receptors, monoclonal or polyclonal antibodies, mono-specific, bi-specific or multi-specific antibodies, monobodies, polybodies.

Further therapeutic active agents may be an antiemetic agent. Suitable antiemetic agents include, but are not limited to, metoclopramide, domperidone, prochlorperazine, promethazine, chlorpromazine, trimethobenzamide, ondansetron, granisetron, hydroxyzine, acetylleucine, alizapride, azasetron, benzquinamide, bietanautine, bromopride, buclizine, clebopride, cyclizine, dimenhydrinate, diphenidol, dolasetron, meclizine, methallatal, metopimazine, nabilone, pipamazine, scopolamine, sulpiride, tetrahydrocannabinols, thiethylperazine, thioproperazine and tropisetron. In a preferred embodiment, the antiemetic agent is granisetron or ondansetron.

In still another embodiment, the other therapeutic active agent can be an opioid or non-opioid analgesic agent. Suitable opioid analgesic agents include, but are not limited to, morphine, heroin, hydromorphone, hydrocodone, oxymorphone, oxycodone, metopon, apomorphine, buprenorphine, meperidine, loperamide, ethoheptazine, betaprodine, diphenoxylate, fentanyl, sufentanil, alfentanil, remifentanil, levorphanol, dextromethorphan, phenazone, pemazocine, cyclazocine, methadone, isomethadone and propoxyphene. Suitable non-opioid analgesic agents include, but are not limited to, aspirin, celecoxib, rofecoxib, diclofenac, diflunisal, etodolac, fenoprofen, flurbiprofen, ibuprofen, ketoprofen, indomethacin, ketorolac, meclofenamate, mefenamic acid, nabumetone, naproxen, piroxicam and sulindac.

In yet another embodiment, the further therapeutic active agent can be an anxiolytic agent. Suitable anxiolytic agents include, but are not limited to, buspirone, and benzodiazepines such as diazepam, lorazepam, oxazapam, clorazepate, clonazepam, chlordiazepoxide and alprazolam.

The term "radiotherapeutic agent" as used herein, is intended to refer to any radiotherapeutic agent known to one of skill in the art to be effective to treat or ameliorate cancer, without limitation. For instance, the radiotherapeutic agent can be an agent such as those administered in brachytherapy or radionuclide therapy. Such methods can optionally further comprise the administration of one or more additional cancer therapies, such as, but not limited to, chemotherapies, and/or another radiotherapy.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication.

Before exemplary embodiments of the present invention are described in greater detail, it is to be understood that this invention is not limited to any particular embodiments described herein and may vary. It is also to be understood that the terminology used herein is for the purpose of describing particular embodiments only, and is not intended to be limiting, since the scope of the present invention will be limited only by the appended claims.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.). . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXAMPLES

The following Examples provide methods for formulating and administering a pharmaceutical composition comprising 5-FU as anti-cancer treatment for colorectal cancer management. These Examples describe materials and methods for making the pharmaceutical composition and demonstrate a sustained-release nanoformulation of FU comprising drug-polymeric coating and sedimentation of insoluble gel formulations as an orally administered colon-targeted chemotherapy. The 5-FU-carrageenan (CRG-FU) coated particles are prepared by kneading/wet granulation. The physiochemical characterizations elucidate the physical and chemical interactions, the crystallinity of the powder and thermogram differences compared to the raw materials. The CRG-FU particles are encapsulated in aqueous hydrodynamic gel of sodium alginate (NA) of high molecular weight grade with CRG-lambda ($CRG_L$) in excess to from a suspension. The optimum suspension was identified based on performance, core character, surface charge, surface character, size and morphology. The nanosuspension was characterized using UV-spectroscopy, zeta-sizer, particle size analyzer and scanning electron microscopy. The analytical results are illustrated in FIGS. 1-13. Additional details can be found in the section entitled "Brief Description of the Drawings".

Example 1

Figure 2:
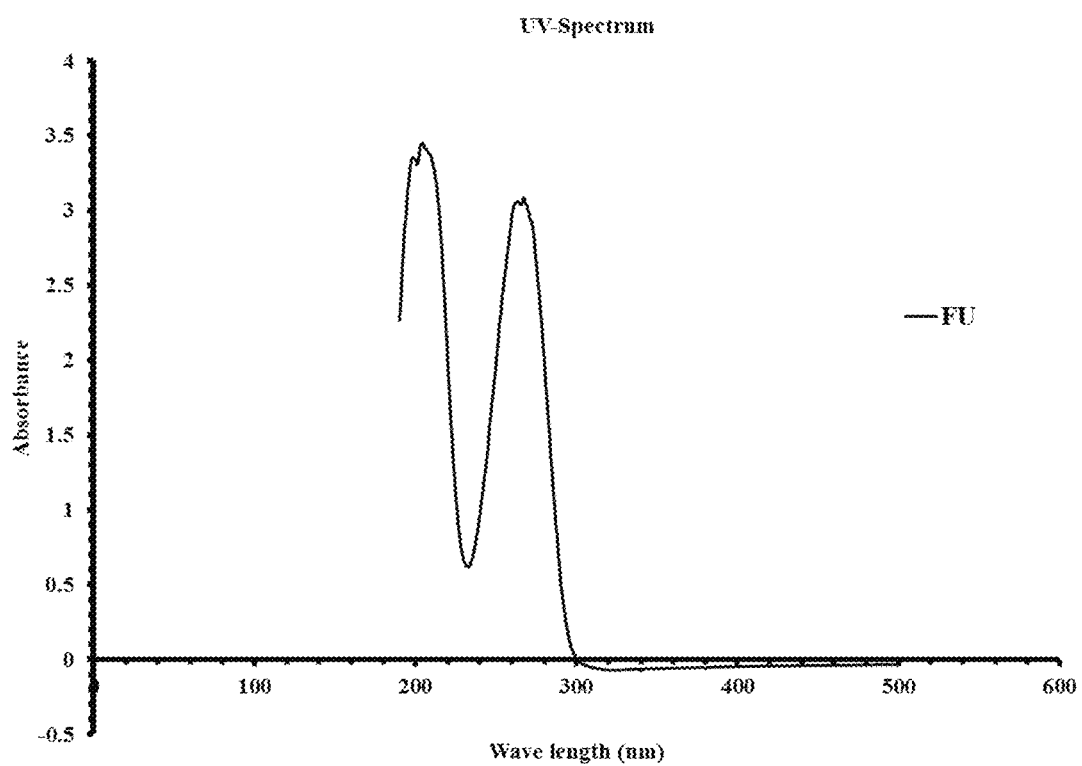
FIG. 2 shows a 5-FU UV-spectrum.
Figure 3A:
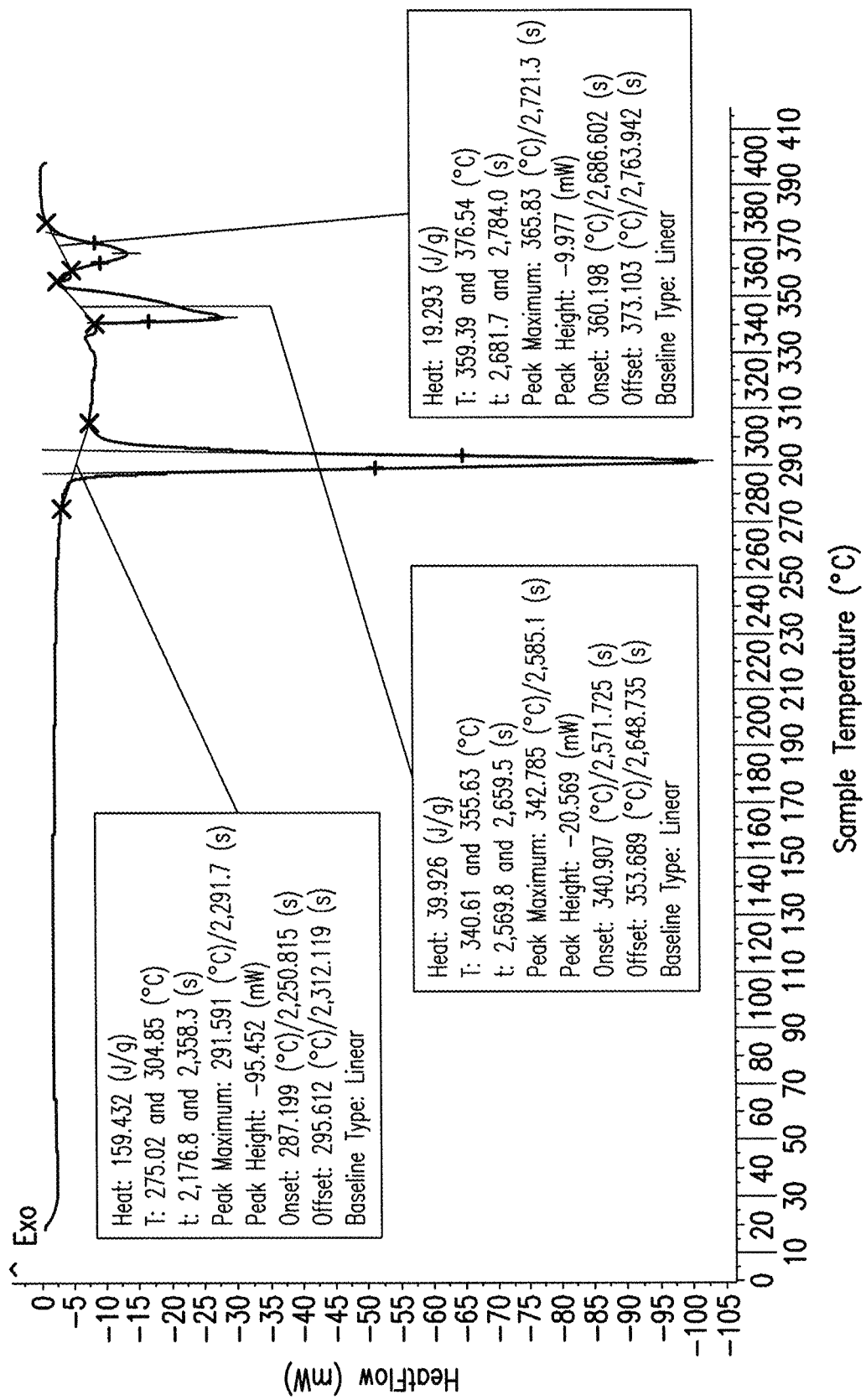
FIGS. 3A-3D show thermograms of DSC for (3A) 5-FU, (3B) CRG, (3C) a physical mixture of 5-FU and CRG, and (3D) a CRG-FU coated particle (Coppt) or kneaded product.
Figure 3B:
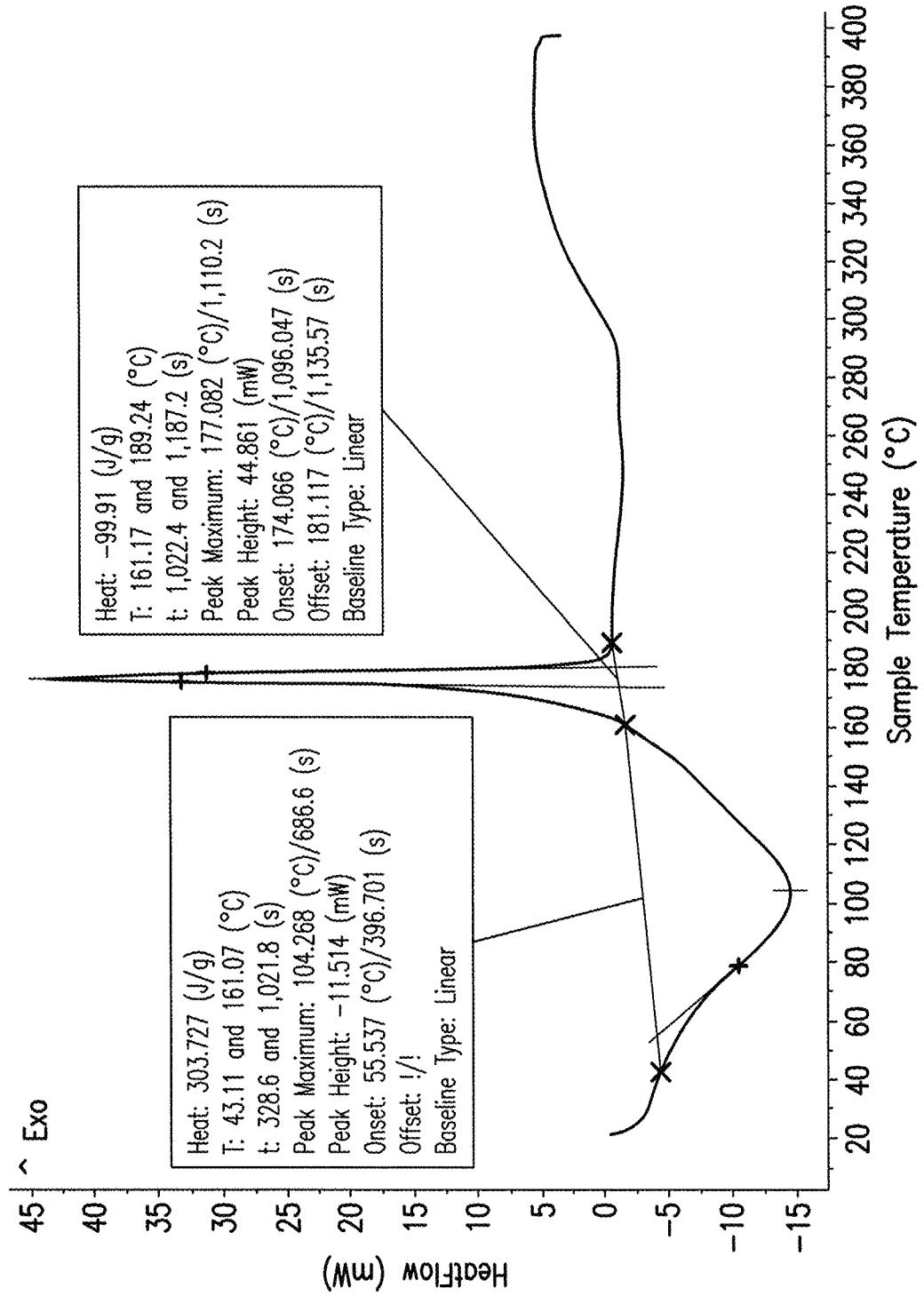
Figure 3C:
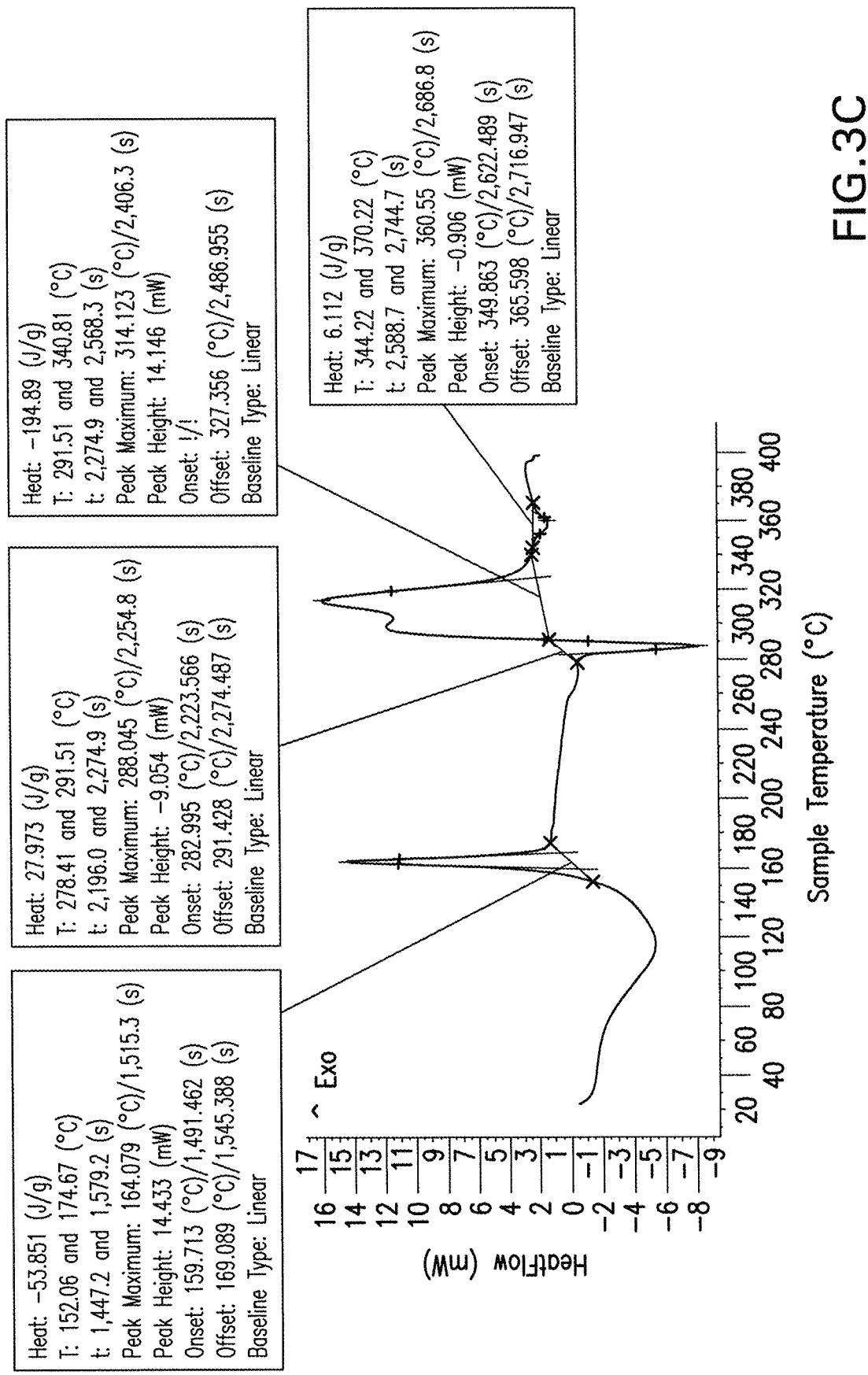
Figure 3D:
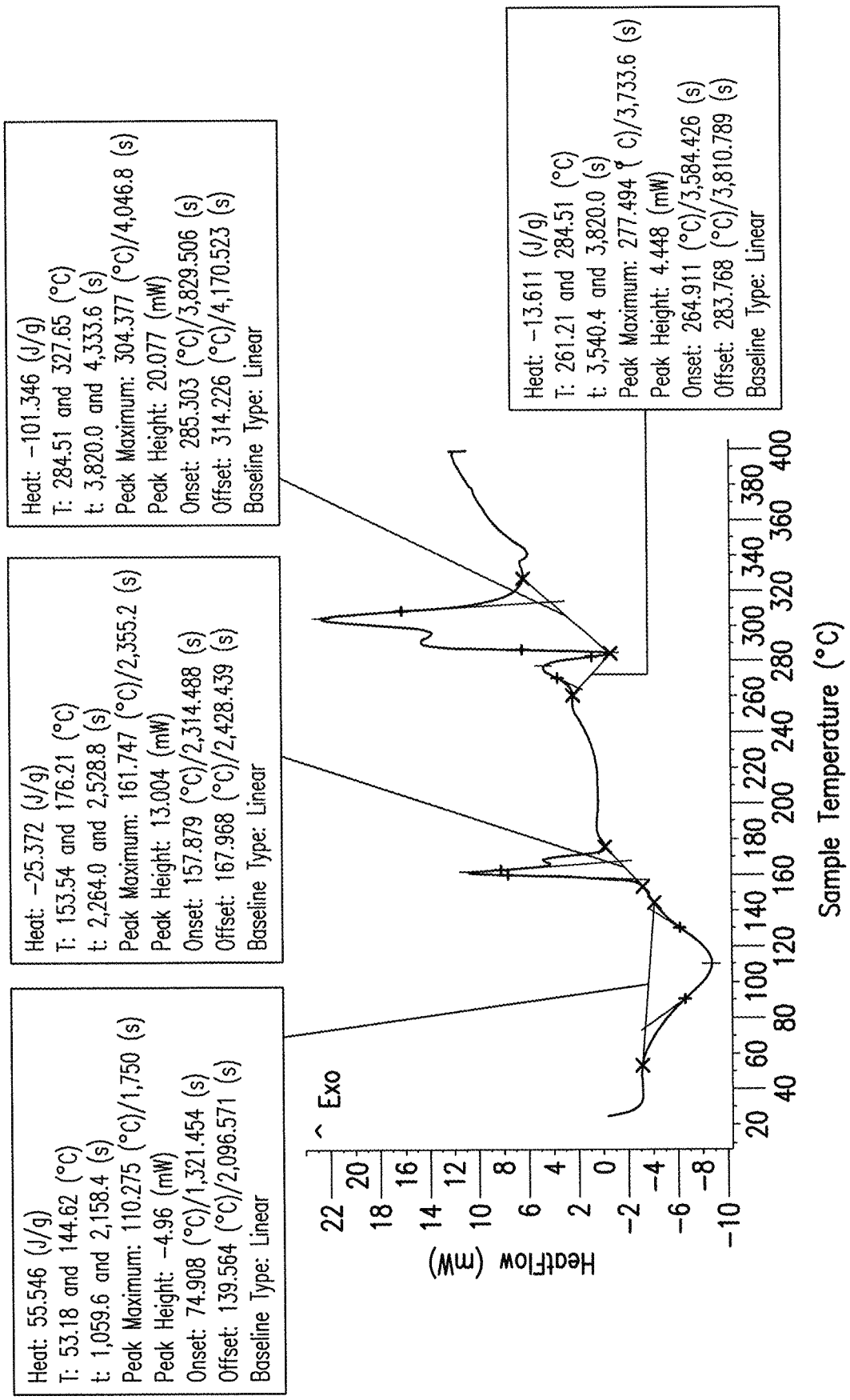

Preparation and Analysis of 5-FU Particles Coated in Carrageenan
Preparation and Analysis of 5-FU Stock Solution A stock solution of 5-FU-98% (Sigma-Aldrich, USA) in distilled water of pH 7.4 was subjected to the UV spectrophotometric analysis (Genesys™ 10S UV-Vis, Thermo-Scientific; USA) at a wavelength of 266 nm in a 1 cm cell versus a blank solution consisting of distilled water. Several dilutions were prepared from the stock solution to construct a calibration curve, as shown in FIG. 1. The selection of the λ-max was based on the UV-spectrum obtained from a pure 5-FU solution, as shown in FIG. 2. Two peaks were obtained (211 and 266 nm). The stock solution was used to test various formulations of the gelling nanosuspension.

Determination of CRG-FU for Optimum Coating Ratio

Different physical mixtures of 5-FU and CRG-Kappa ($CRG_k$)—(FMC-biopolymer, USA) were prepared. The combination of 5-FU and CRG formed the particles identified as CRG-FU. A fixed amount of 25 mg-$CRG_K$ was mixed with 6.25, 12, 19, 25, 51 or 77 mg 5-FU using a mortar and pestle. A small amount of distilled water was added to each mixture with levigating. The mixtures were left under the fume-hood for overnight to dry. On the day after, the kneaded CRG-FU mixtures (5-FU particles coated with CRG polymer or (Coppt)) were dissolved with buffer of pH 4. After complete dissolution and centrifugation of the particles, absorbance of the clear supernatant layer was measured for each levigate using UV spectrophotometric analysis at a wavelength of 266 nm. The absorbance was converted to the coated 5-FU concentration (μg/mL) using the calibration curve equation to determine the amount of the coated 5-FU particles. This assay is used to choose the CRG-FU mixture having the optimum CRG coating efficiency, gel hardness, 5-FU loading and the least aggregation of particles. Table 1 shows the results of the coating assay of the kneaded CRG-FU particle products using various ratios of 5-FU/CRG.

TABLE 1

CRG-FU coating assay for the kneaded products.

| 5-FU/CRG ratio | 5-FU loaded amount (mg) | Total amount 5-FU and CRG (mg)* | Coated 5-FU amount (mg) ± SD (n = 3) | Coated 5-FU/Total CRG (mg/mg)* |
|---|---|---|---|---|
| 0.25 to 1 | 6.25 | 31.25 | 6.21 ± 0.04 | 0.25 |
| 0.5 to 1 | 12.00 | 37.00 | 11.95 ± 0.05 | 0.48 |
| 0.75 to 1 | 19.00 | 44.00 | 18.00 ± 0.03 | 0.72 |
| 1 to 1 | 25.00 | 50.00 | 24.89 ± 0.04 | 1.00 |
| 2 to 1 | 51.00 | 76.00 | 49.90 ± 0.05 | 1.96 |
| 3 to 1 | 77.00 | 102.00 | 75.02 ± 0.05 | 3.00 |

*CRG amount is 25 mg.

The results tabulated in Table 1 represent a linear coating without adsorption of the FU inside the CRG gel upon levigating. The drug crystals were left to be dried inside the gel. Thus, FU crystals were coated by the CRG polymer. Many factors were considered in order to decide which of the FU-CRG ratios might be chosen to be used inside the formula. The ratio of 25 mg FU and 25 mg CRG (1:1) resulted in optimum drug loading amount, gel hardness, coating and homogenization efficiency with minimum FU aggregation of crystals.

Preparation of CRG-FU Coated Particles

Mixtures of (1:1) 5-FU and $CRG_k$ were prepared using the coating assay described in the previous step. Using an ERWEKA coating pan (DKE/DKS, Germany) and the levigating and kneading method or a wet granulation method, equal amounts of 5-FU and $CRG_L$ or CRGκ ($CRG_L$-high molecular weight of 788.7 g/mole-750 mPa, viscosity in 1.5% water solution/FMC-biopolymer, USA) were sprayed with distilled water after physical mixing. The gel product was transferred and flattened on a glass plate. It was left under the fume-hood for overnight to dry. On the day after, the dried gel product comprising a film of coated particles CRG-FU (Coppt) was collected and sieved to reduce the particle size and insure a particle size of less than 250 μm.

Characterization and comparison of the CRG-FU coated particles (Coppt), 5-FU alone, CRG alone, and a physical mixture of 5-FU and CRG (without kneading or levigating) were conducted using the following techniques.

Differential Scanning Calorimetry (DSC)

Powder samples were weighed and scanned in sealed 120 μl aluminum crucibles with pierced covers over a 25-400° C. temperature range. The heating rate was 10° C./min using SETARAM Instrumentation DSC 131 evo equipment (KEP Technologies, France). Instrument calibration was performed using indium. Thermograms were recorded under nitrogen purge (30 mL/min).

As shown in FIG. 3A-3D, the peaks of the thermal transitions were integrated for their heat value (J/g), range of each peak, offset and onset (temperature, ° C. and time, seconds), peak height (mW) and temperature of the peak maximum. The thermogram of 5-FU (FIG. 3A) shows sharp three endothermic peaks (290, 347.5, 367.5° C.). These peaks could be a result of melting and/or polymorphisms. The sharpness of the peaks was crystallization, an indication of the 5-FU powder (Sekhar et al. 2011). The $CRG_k$ thermogram (FIG. 3B) was distinctive of broad endothermic peak (43-161° C.) that was a result of moisture loss and/or conformational change of the polymer. The $CRG_k$ thermogram had a sharp exothermic transition at 177° C. This was due to thermal degradation of the polymer (Abd-Elbary et al. 2012 *Pharmaceutical Development and Technology*. 17(5): 562-573.). The physical mixture thermogram (FIG. 3C) of equal amounts of 5-FU and $CRG_k$ had sharper endothermic peak temperature for $CRG_k$ peaks (endothermic: 66-150° C.) and shifting down of the thermal degradation peak (164° C.). This might be a result of the physical mixing of $CRG_k$. Regarding the FU endothermic peaks, two of them were approximately the same of the pure FU (288 and 360° C.). An additional exothermic peak of FU at 314° C. was absent, which may be due a late thermal degradation of $CRG_k$ in the physical mixture. The coated particles CRG-$FU_k$ thermogram (FIG. 3D) showed sharper $CRG_k$ endothermic peaks, indicating crystallization (74.9-144.6° C.), shifting down of the $CRG_k$ exothermic peak (161.747° C.) and with additional two exothermic peaks (277.5 and 304° C.) of late $CRG_k$ degradation as a result of physical dispersion for $CRG_k$ around 5-FU using water. This thermogram did not show any of the 5-FU endothermic peaks. This might be indication of the 5-FU thermal degradation happened with $CRG_k$ thermal degradation at 161.747, 277.5 and 304° C. The coated particle thermogram provides validation of the coating process for the 5-FU particles with the $CRG_k$ during the kneading process.

Chemical Structures and Interactions Characterization

Direct sampling of solid or liquid in the sample well was performed using a Nicolet™ iS™ 10 FTIR Spectrometer (Thermo-Scientific, USA). Each sample was compressed using the stainless-steel pin of the instrument. The sample was scanned at laser frequency of 15798.7 cm-1 and medium resolution.

Figure 4A:
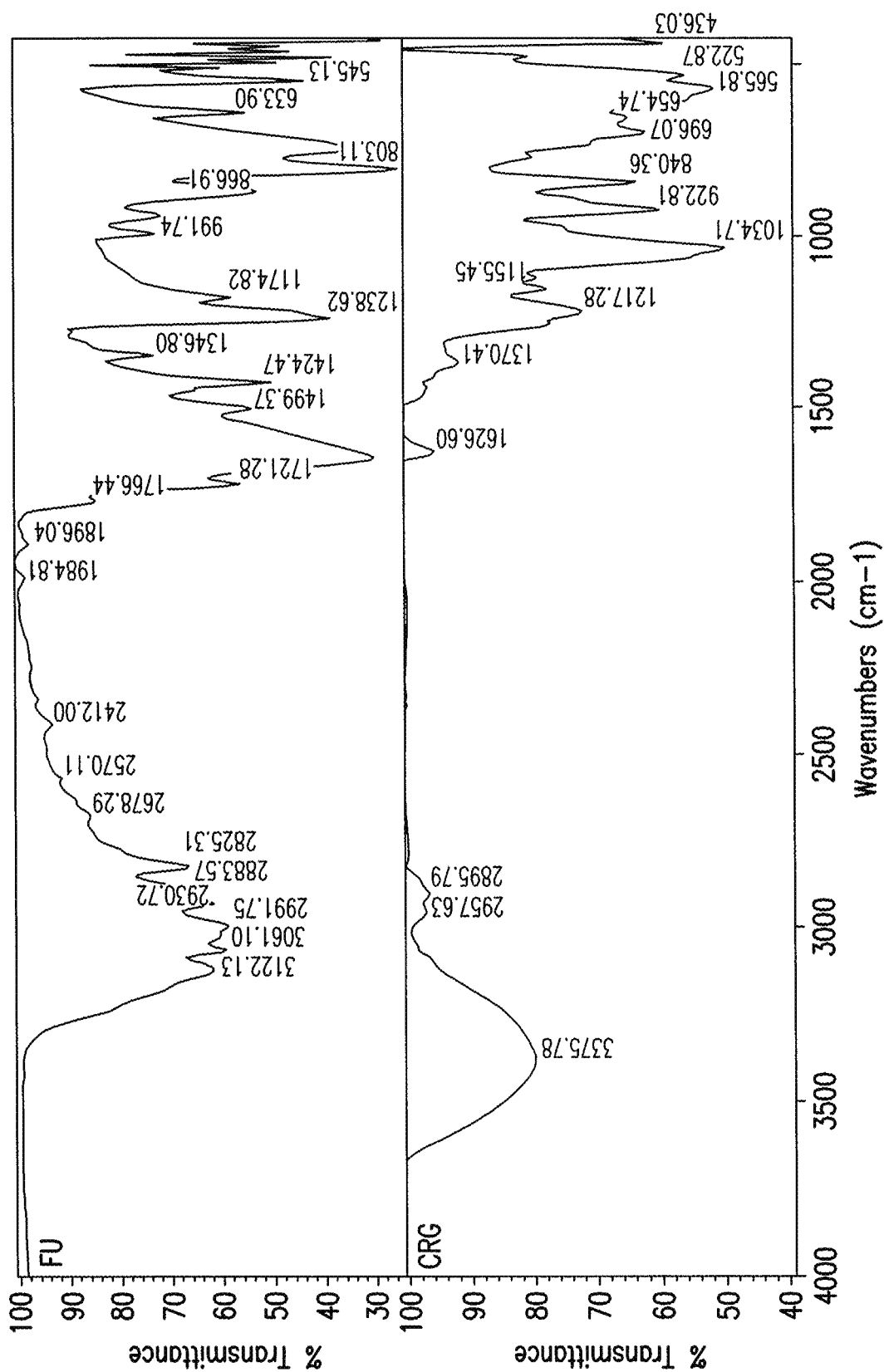
FIGS. 4A and 4B show FTIR spectra for (4A) 5-FU, (4B) CRG, (4C) a physical mixture of 5-FU and CRG, and (4D) a CRG-FU coated particle (Coppt) or kneaded product.
Figure 4B:
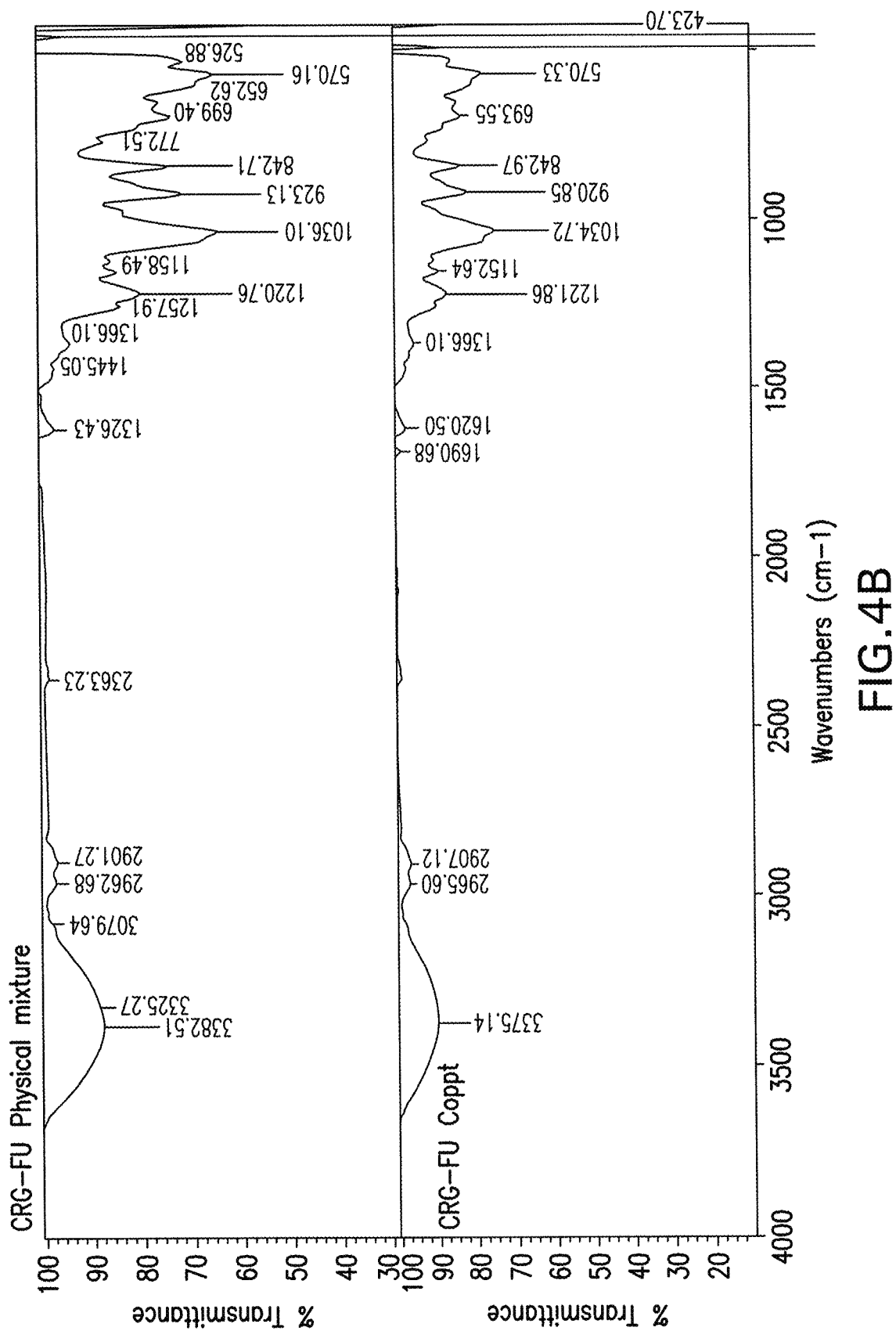

FIG. 4A illustrates the spectra of the pure 5-FU (Right/upper) and $CRG_k$ (Left/lower) in FIG. 4A, and FIG. 4B illustrates the physical mixture (Right/upper) and the CRG-FU coated particles-Coppt (Left/lower). For pure 5-FU, the absorption bands at 1721.28, 1672, and 1238.62 $cm^{-1}$ were responsible for cyclic imide, CO—NH—CO, imide, amide I band (C═O), and amide III band (C═O), respectively (Lin et al. 2002 *Biomaterials*. 23(9):1981-1987). The $CRG_k$ main vibrations were ranging at 3100 to 3800 $cm^{-1}$ (hydroxide stretch), 2957.63 cm$^{-1}$ and 2895.79 cm$^{-1}$ (carbon-hydrogen bond stretch), 1626.6 cm$^{-1}$ and 1370.41 cm$^{-1}$ (carbon-hydrogen bond deformation), 1230 cm$^{-1}$ (sulfate ester salt's sulfoxide double bonds vibration), 1034.71 cm$^{-1}$ (vibration of cyclic ethers 'carbon-oxygen single bond) and 922.81 cm$^{-1}$ (carbon-oxygen single bond vibration of hydroxyl groups attached to carbons) (Signoretti et al. 1988 *Drug Development and Industrial Pharmacy.* 14(9):1167-1184). In common CRG$_k$ and 5-FU, the physical mixture spectra had main peaks with lower intensity of absorption because of the dilution effect. The CRG-FU Coppt spectrum showed the all CRG$_k$ peaks with only one peak corresponding for 5-FU (1690 cm$^{-1}$-amide I band (C=O)). The previous spectrum validates the CRG$_k$ coating of the 5-FU due to the fact that the FTIR spectra illustrate the chemical bond vibration of the surface molecules. This result was consistent with DSC result. These findings also support the conclusion of oral safety, bioavailability and the ability of the formula to encapsulate the 5-FU and protect it from the metabolic enzymes.

Characterization of Crystallinity

A high-resolution MAXima X SRD-7000 X-ray diffractometer (Shimadzu, Japan) was used with a Cu anode and 2.2 kW tube ($\lambda$=1.54° A) at 40 kV and 40 mA. The scanning speed of 5-80°/min was achieved.

Figure 5A:
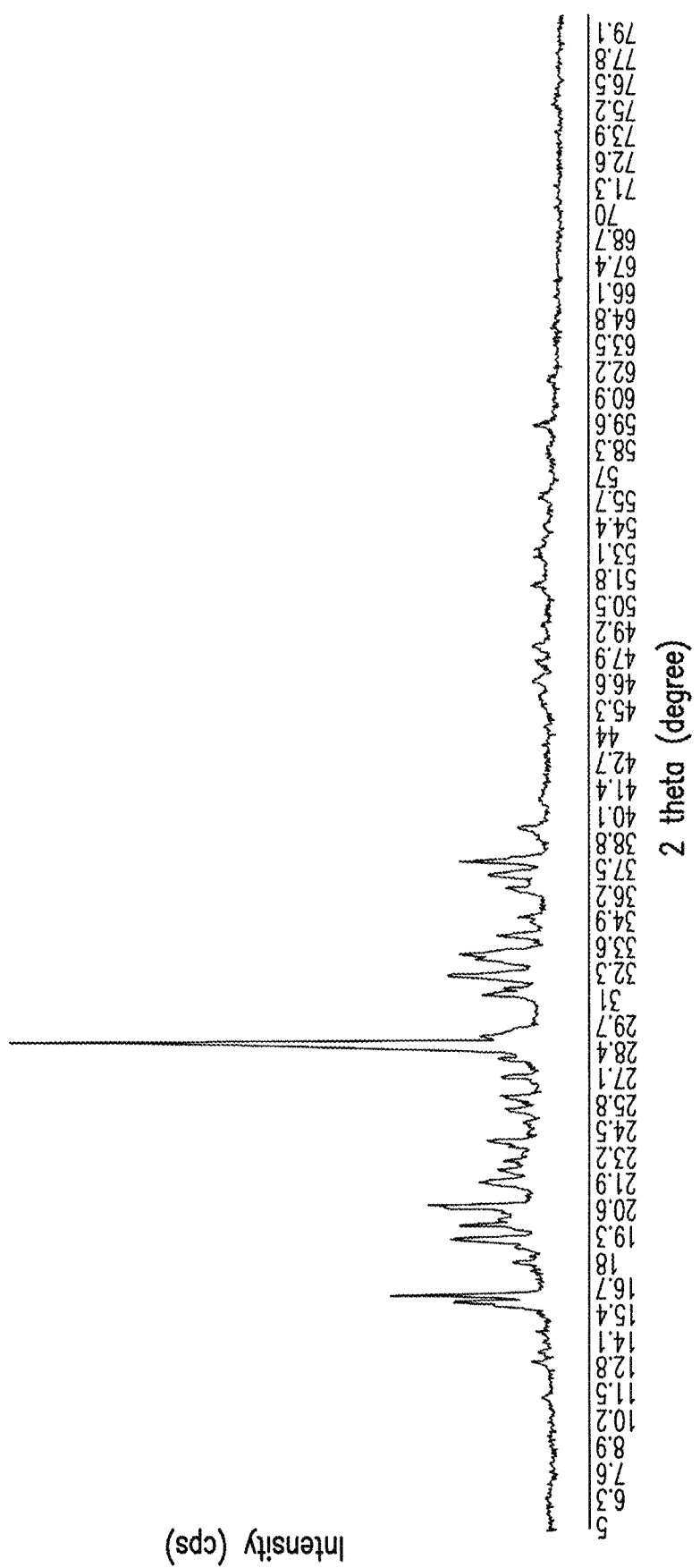
FIGS. 5A-5D show diffractograms of PXRD for (5A) 5-FU, (5B) CRG, (5C) a physical mixture of 5-FU and CRG, and (5D) a CRG-FU coated particle (Coppt) or kneaded product.
Figure 5B:
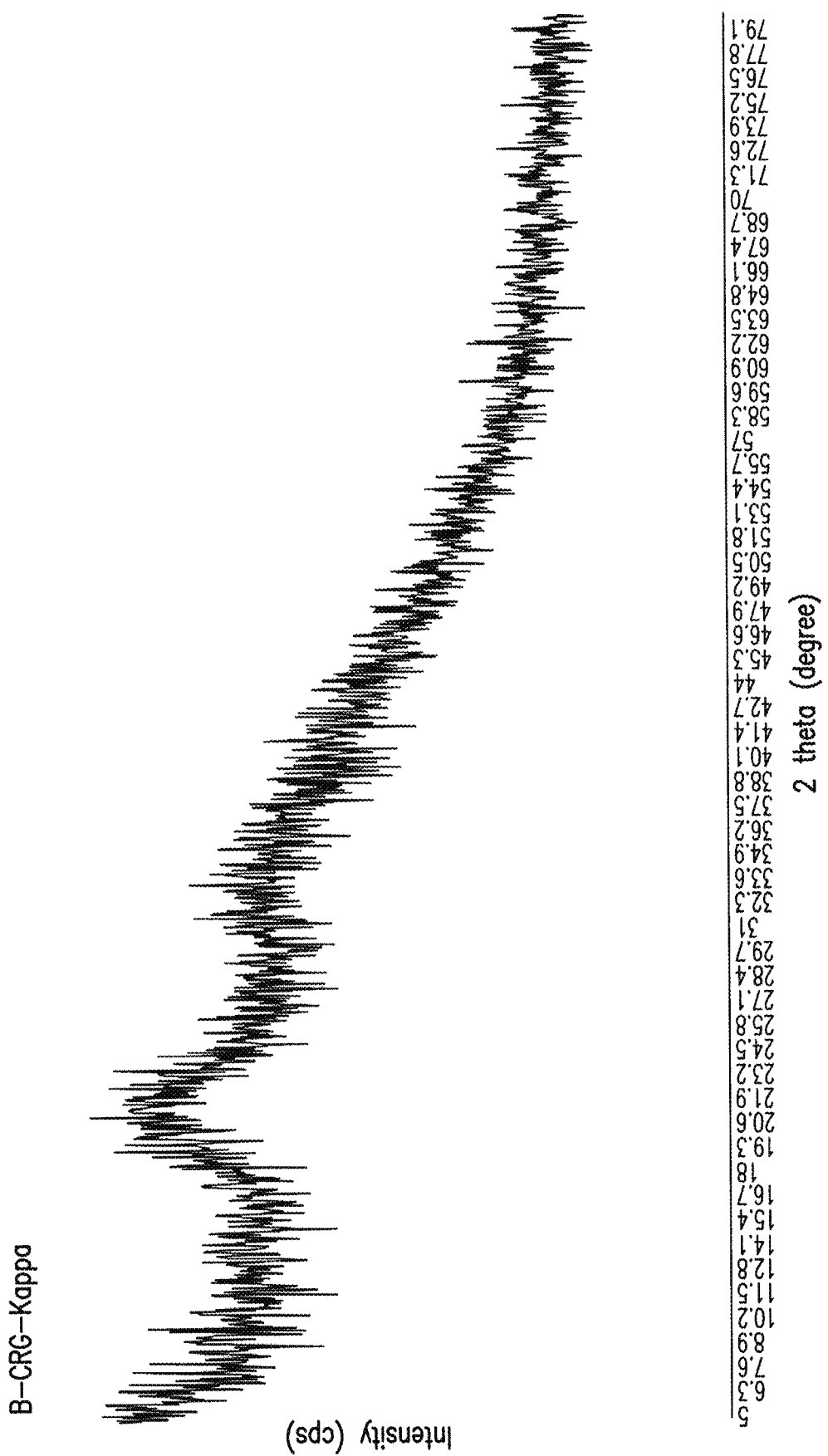
Figure 5C:
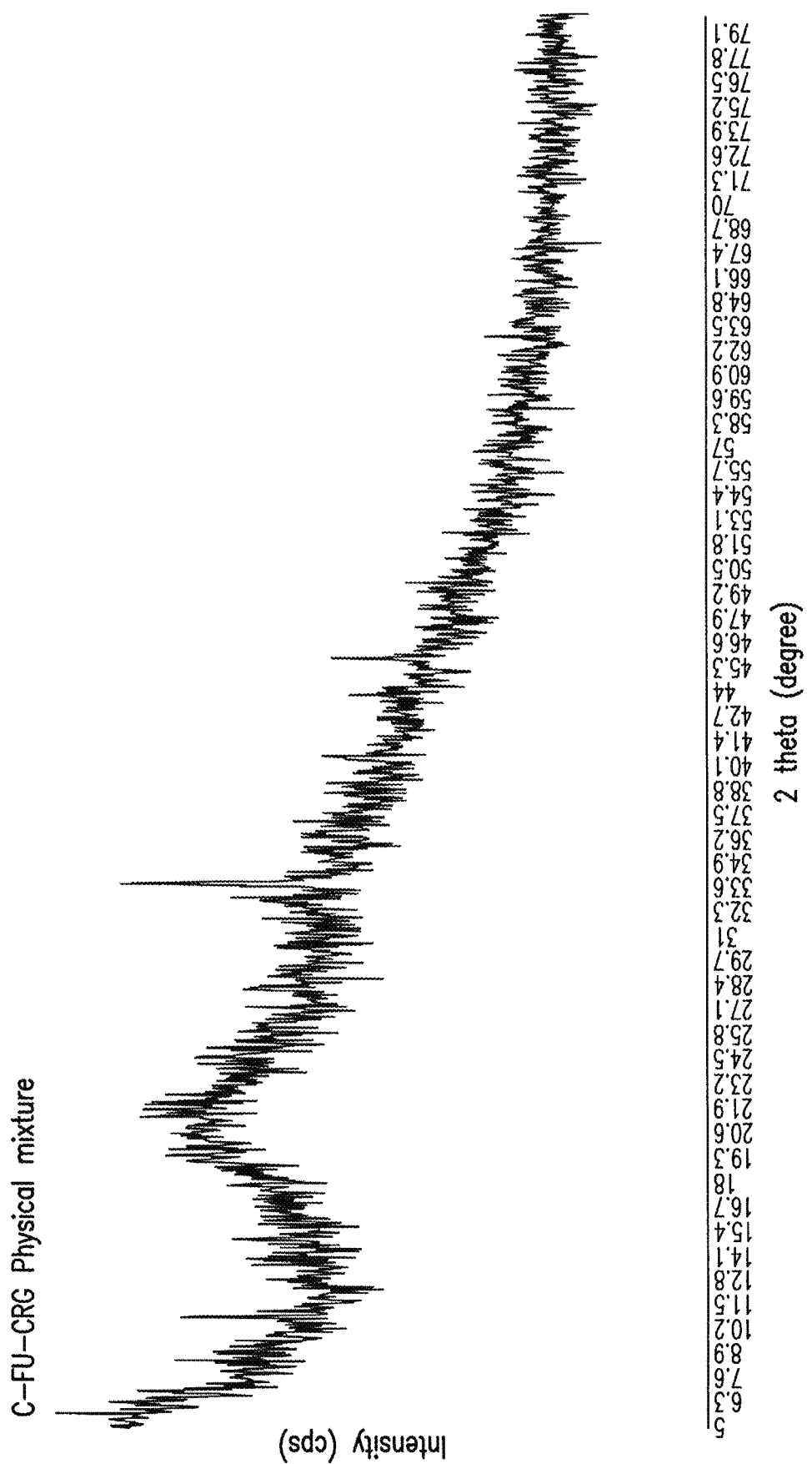
Figure 5D:
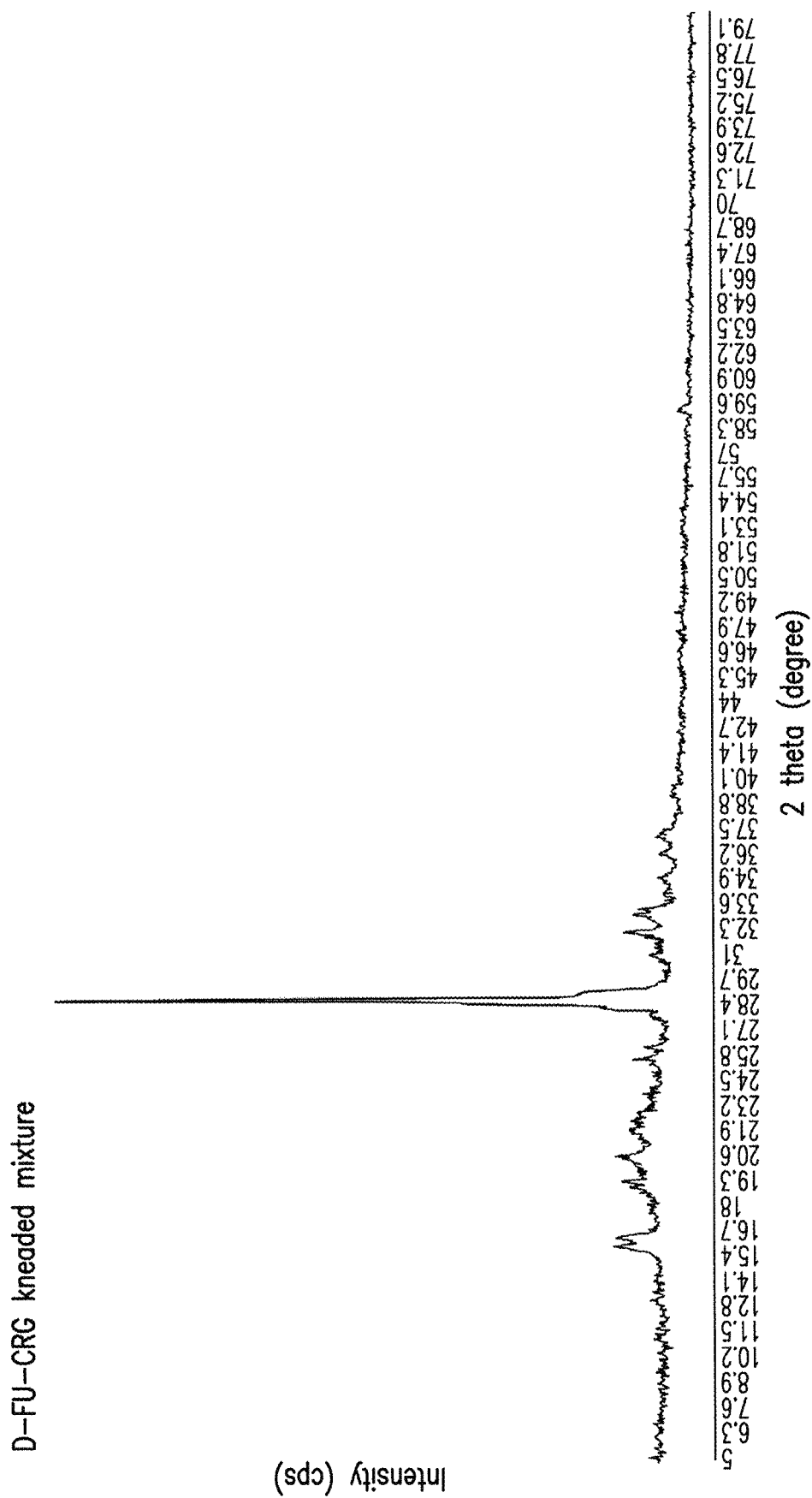

The diffractograms are shown in FIGS. 5A-5D. In FIG. 5A, 5-FU showed specific diffraction peaks in the range of 15.4°-37.5° as crystalline powder. The CRG$_k$, shown in FIG. 5B, did not present characteristic diffraction patterns as an amorphous powder in the 2θ range of 5°-80°. In the physical mixture of 5-FU and CRG$_k$, shown in FIG. 5C, some 5-FU peaks presented with at lower peak intensity due to the dilution effect. The physical mixture also appears to be amorphous, as was the CRG$_k$ diffraction. Compared to the physical mixture, the coated particles of CRG-FU, shown in FIG. 5D, appear in the range of 15.4°-33.6° to have distinctive crystal peaks that were similar to 5-FU pure peaks along with no distinctive peaks (amorphous) above and below the range of 15.4°-33.6°. Taken together with the results of the DSC and FTIR, these data demonstrate that the CRG$_k$ coated the 5-FU in the preparation of CRG-FU, thus preserving some of the drug crystallinity. This preparation will contribute to retarding the dissolution rate for CRG-FU particles due to the crystal structure and growth (Sunagawa 1994. Chapter 2 in: Wolf K H, Chilingarian G V, editors. *Developments in Sedimentology*. Elsevier; p. 19-47).

Example 2

Preparation of CRG-FU Gelling Nanosuspension
Overview

The optimization process of the formulation used various gel characterizations and in vitro drug release studies to evaluate the formulation of component factors. The results of these characterizations and studies were used to determine the optimum parameters that would provide a sustained-release system. These assessments of the onset and extent of gelling were critical to forming the insoluble gel upon the contact with the gastric media. In addition, the criteria were established so that development of the gel would be compatible with rapid or fast gastric emptying of the gel, i.e., movement of the pharmaceutical composition through the stomach. Without being bound by theory, the sedimentation of the insoluble gel stimulates gastric emptying, and is thus a useful characteristic that contributes to the design of the formulation. The goal was to shift the 5-FU release to the intestinal and colonic area of the target site (i.e. colon cancer) and to minimize early release of the 5-FU in the stomach which would result in gastric adverse effects.

In this Example, a therapeutically effective amount of 5-FU is used to prepare a single dose of the gelling nanosuspension for oral administration. Per the NCCN Guidelines 2019®, the standard dose for a chemotherapy treatment of 5-FU is 20 mg/Kg*m$^{-2}$ of body weight or 1200 mg/m$^2$ of body surface area. This dose is typically prescribed as the amount given in a weekly administration.

As disclosed in the previous Example, a 1:1 mixture of 5-FU and carrageenan is used to prepare CRG-FU coated particles (Coppt) by kneading and levigating. Suitable amounts of CRG-FU particles with CRG solution (2%) were placed into glass beakers. This was followed by homogenization for 1 min with magnetic stirring. The homogenized mixture was added to a 6% NA solution and mixed for 15 min using a stirrer (ERWEKA PRS Planetary Stirrer, Germany). 72 mg/mLKg$^{-1}$ NA was determined to be the optimal amount for a formulation that produced an insoluble gel at a low pH. The maximum safe dose of NA was 40,000 mg/Kg in compliance with the European Food Safety Authority-2008. CRG amount was 5 mg/mLKg$^{-1}$ to be partitioned for coating or free CRG and considered safe (Zhou et al. 2005 *Pharmacological Research.* 51(2):153-157, Bani-Jaber and Abdullah 2020 *Pharmaceutical Development and Technology.* 25(6):666-675).

After drying, the particles are suspended as NAH-CRG-FU, in which NA (HMWT grade of 595,000-600,000 g/mole) has a viscosity of 638 to 640 mPa·s in 1% water solution (Sigma-Aldrich, USA). The excess CRG in the nanosuspension serves as mixed polymeric gel former with the excess NA, and these provide further retardant of CRG-FU Coppt dissociation in the nanosuspension.

Table 2 shows the nanosuspension components of NAH-CRG-FU and free 5-FU. The free 5-FU has a concentration of 1 mg/ml in an aqueous solution.

TABLE 2

Composition of gel-forming aqueous formulation of NAH-CRG-FU or 5-FU.

| Component | NA-level (mg/mL) | CRG* (mg/mL) | Coated or Free 5-FU | Coating CRG |
|---|---|---|---|---|
| NAH-CRG-FU | 72 | 4 (Lambda) | Coated | CRG-Kappa |
| Free 5-FU | — | — | Free | — |

*In excess of CRG$_k$-FU coated particles.

Example 3

Demonstrations of Drug Release, Insoluble Gel Formation and Sedimentation
Preparation of NAH-CRG-FU Gelling Nanosuspension The ultimate goals were to develop a formula with in-soluble gel forming ability in the gastric media with good coherence, to form a sedimented gel with a density >1 in the stomach, to increase the gastric emptying rate and to avoid the gastric adverse effects and metabolism of FU by keeping a minimal gastric release or coating it. On other hand, the formula needed to dissolve and release the drug and gel in the simulated intestinal media, especially the colonic area. The main target was to design a system that was able to inhibit release of the drug in the stomach (i.e., release at a lower rate than the release rate in the intestinal-colonic area). Formulation was prepared according to Table 2 and the pattern of 5-FU release in the pH-profile differed from that of free 5-FU. After preparation of different formulations with manipulation of NA amounts (18, 36 and 72 mg/mL) and CRG types ($CRG_K$ and $CRG_L$), the drug release optimization confirmed that the optimum formulation with respect to FU release curve and parameters was the NAH-CRG-FU shown in Table 2 and FIG. 6. Thus, the optimum formulation was found to have minimum release in the simulated gastric media (pH 1.2) and a sustained-release pattern in the simulated intestinal-colonic media (pH 6.5, 6.8 or 8). The comparisons between the release patterns of the NAH-CRG-FU formulation and free drug were done using the simulated gastric release percentage (%)—first 2 hrs, simulated intestinal-colonic release percentage-subsequent 6 hrs (summation of the proximal, distal intestine and colon percentage simulated release patterns), mean dissolution time (MDT) of simulated pre-intestinal region (gastric) and simulated intestine-colonic area. Furthermore, mean dissolution times for $1^{st}$ 2 hrs of pre-intestinal (Pre-intestinal MDT) and from the 2nd to 8th hr of the release profile (Intestinal-colonic MDT) were obtained by the following equation (Bani-Jaber and Abdullah 2020, Costa and Lobo 2001).

$$MDT = \frac{\sum_{i=1}^{n} t_{mid} \cdot \Delta M}{\sum_{i=1}^{n} \Delta M}$$

wherein (i) expressed the release sample numbers, (n) referred to the number of release times, (t) was the mid-point time in the interval ($t_{i-1}$–$t_i$), ($\Delta M$) was the released amount of drug in the interval ($t_{i-1}$–$t_i$). The MDT larger values could indicate a slower drug release rate. The predicted rate of release equates to the rate of dissolution, and this rate has a direct effect on the number of daily oral doses and any adverse effects associated therewith.

5-FU was prepared in a formulation of the NAH-CGR-FU gelling nanosuspension, as described in the previous Examples. Data from Table 2 was used to prepare a nanosuspension volume of 20 mL. The dose was loaded into a dialysis bag having a cut-off of 12000-14000 Dalton (Spectra/Por® 4-Dialysis membrane, USA). The dialysis bag was placed into a beaker containing 300 mL of release media. The bags were exposed to 0.1N HCl to simulate gastric media having a pH 1.2 for 2 hr, followed by simulated proximal intestine media, which was a phosphate buffer with pH 6.5 for 2 hr. This was followed by media simulating the media of the distal area of the small intestine, which was a phosphate buffer at a pH 6.8 for 2 hr. Finally, the dialysis bags were transferred to a phosphate buffer media having a pH 8 to simulate the media of a descending colon for 2 hrs. The sequential exposure in the different pH media was used to construct a pH dissolution profile. The temperature was constantly controlled at 37±0.5° C. in a water bath shaker of 75 rpm speed. To maintain sink conditions, the dissolution media underwent total replacement with a fresh medium every hour. After drug release optimization of the NA amount and CRG type was determined, the optimum formulation in-soluble gel that was formed in the acidic media was evaluated for the onset of formation and the extent of sedimentation.

In Table 3, the calculated drug-release parameters for HAH-CRG-FU nanosuspension and free 5-FU are shown.

TABLE 3

| Drug release parameters | | |
|---|---|---|
| | NAH-CRG-FU | Free 5-FU |
| Pre-Intestinal MDT-(hr)* | 0.90 ± 0.0017 | 0.23 ± 0.0011 |
| Intestinal-Colonic MDT-(hr)* | 4.69 ± 0.0071 | 1.75 ± 0.0051 |
| Gastric % Release* | 25.05 ± 0.0031 | 56.60 ± 0.0051 |
| Proximal Intestine % Release* | 6.30 ± 0.0036 | 23.04 ± 0.0022 |
| Distal Intestine % Release* | 2.01 ± 0.0021 | 9.08 ± 0.0019 |
| Colon % Release* | 0.39 ± 0.0031 | 7.26 ± 0.0014 |
| Gastric % Release* | 25.05 ± 0.0031 | 56.60 ± 0.0051 |
| Intestinal-Colonic % Release* | 8.69 ± 0.0044 | 39.37 ± 0.0071 |

*For n = 3 ± standard deviation

Figure 6:
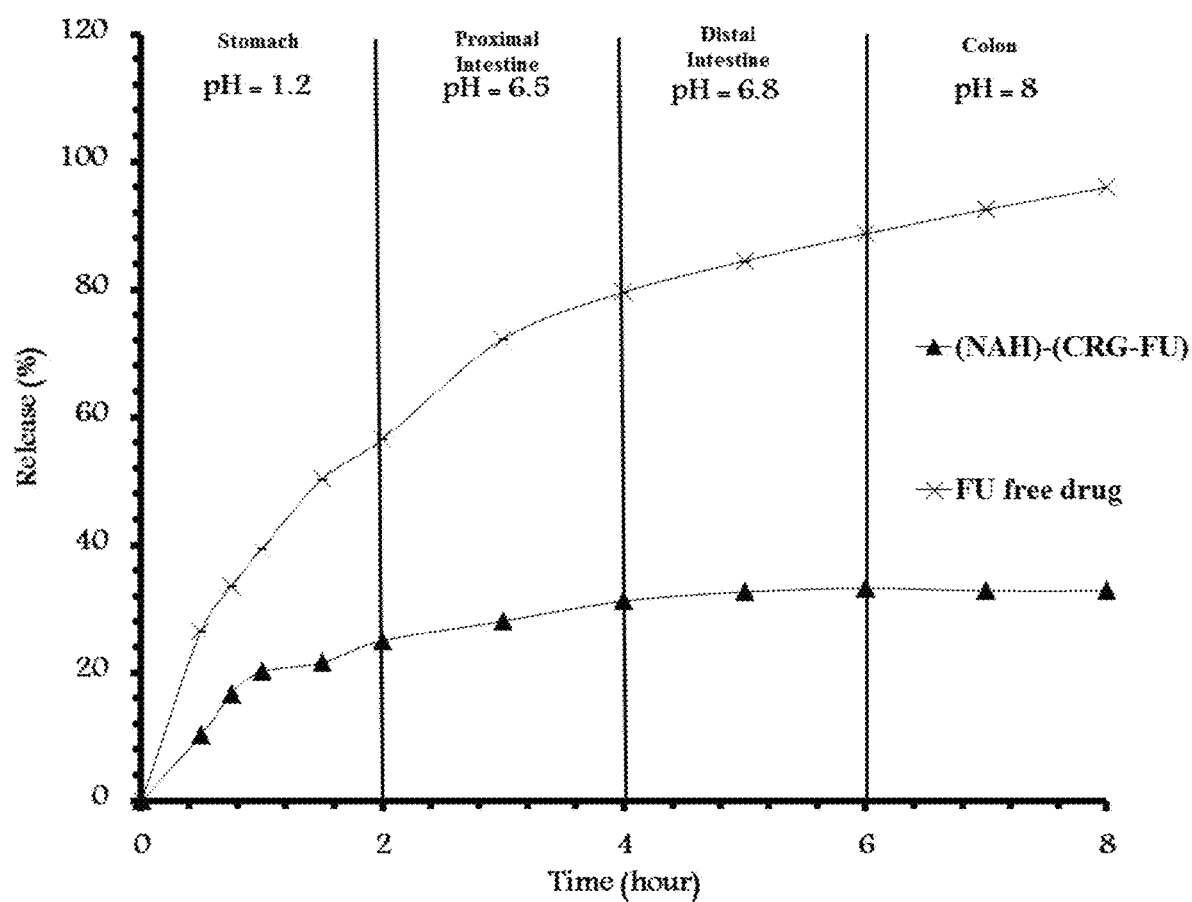
FIG. 6 shows drug release pH profiles of NAH-CRG-FU and free FU.

5-FU as free drug compared with NAH-CRG-FU suspension is also shown FIG. 6. Free 5-FU showed higher gastric percentage release than NAH-CRG-FU by 31.55% and higher intestinal-colonic percentage release than NAH-CRG-FU by 30.68%. The overall pH-profile percentage release using 5-FU free was more than NAH-CRG-FU suspension by 62.2% and this was consistent with MDT results. This finding was the original goal that was achieved in this formulation.

Each of the ingredients in NAH-CRG-FU was considered key players in sustaining the drug release, especially HMWT NA. The $CRG_K$ was used to decrease the 5-FU solubility and availability to cells and metabolic enzymes. Excess $CRG_L$ was used to capture the released 5-FU and strengthen the alginic acid gel. NA was the encapsulating matrix to control and target the release location of the 5-FU release, depending on the pH of the gastrointestinal tract. The rest of 5-FU in NAH-CRG-FU that was not released after 8 hrs of the drug release study (66.26% remaining drug in NAH-CRG-FU) would be available to be released in the next 22-70 hours of colon residency time. The time of colon residency is varying based on many factors (see Amidon et al. 2015. *AAPS Pharm Sci Tech* 16(4):731-741.). One factor is that the presence of a colon cancer or irritable bowel disease might shorten the time to 24 hrs. 95.97% of free 5-FU was released after 8 hrs of the pH-profile study.

In preliminary studies of NA-containing sustained release 5-FU formulations, the release of the optimum suspension NAH-CRG-FU in the simulated gastric media for the first two hrs was in a slow release manner and not more than ¼ of the FU dose encapsulated compared to similar or higher percentage of FU released as a burst in contact of 0.1N—HCl from the previous formulations mentioned in the literature. Additionally, the release from this formulation at pH 6.8 was in a slow release pattern and lower than the release of previously published FU-SR formulations based on NA by 30-50% (McCarron et al. 2000, Arica et al. 2002, Shishu et al. 2007, Patel et al. 2008, Olukman et al. 2012, Manjula et al. 2013, Sun et al. 2019, Dalei et al. 2020). This suspension had been studied for release over pH-profile (1.2-8) but the previous studies did not study the release over this pH-profile.

Figure 7:
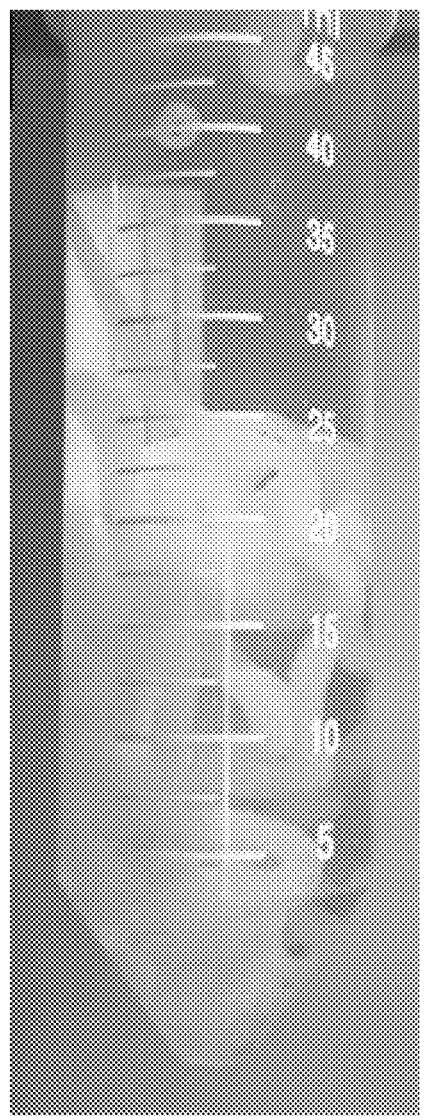
FIG. 7 shows the sedimenting gel formed after 0.5 hr of NAH-CRG-FU in 0.1N HCl.

Along with the drug release testing, NAH-CRG-FU was tested to form an insoluble sedimented gel upon the contact with the simulated gastric medium (0.1 M HCl). The insoluble gels were tested to maintain their integrity after 2 hrs in a simulated gastric medium in the gel characterizations study-durability testing. The sedimentation of the gel was found to be dependent upon the NA molecular weight and concentration. The NAH-CRG-FU suspension met the goals of the 5-FU formulation after gel sedimentation results, as illustrated in FIG. 7 and Table 4, drug release results and gel characterizations in the subsequent sections.

However, the physical form of the gel was a coherent threadlike structure for NAH-CRG-FU. The gel strength was dependent on MWT NA and concenctration of NA (Signoretti et al. 1988).

TABLE 4

General characterization of the gel in optimum formulations.

| Formulation | Formation Speed | Flotation or Sedimentation | Coherence |
|---|---|---|---|
| (NAH)-(CRG-FU) | Immediate | Sedimentation | Good |

Aging Influence on Drug Release

The optimum suspension NAH-CRG-FU was freshly prepared and stored in amber glass bottles at room temperature. The suspension drug release was performed after 2 and 4 weeks. The test was made using the pH-profile of dialysis bag method as described in the previous method. Results of the aging influence on formulation on FU release is shown in Table 5.

TABLE 5

Drug release parameters for NAH-CRG-FU aging.
n = 3, ± standard deviation

| Comparison of Percentage Release | NAH-CRG-FU At day 1 | NAH-CRG-FU 2 weeks | NAH-CRG-FU 4 weeks |
|---|---|---|---|
| Gastric Release | 25.05 ± 0.0031 | 30.28 ± 0.0061 | 57.48 ± 0.0017 |
| Proximal Intestine Release | 6.30 ± 0.0036 | 6.50 ± 0.0037 | 12.30 ± 0.0011 |
| Distal Intestine Release | 2.01 ± 0.0021 | 2.83 ± 0.0031 | 5.03 ± 0.0071 |
| Colon Release | 0.39 ± 0.0031 | 0.45 ± 0.0011 | 2.01 ± 0.0031 |
| Gastric Release | 25.05 ± 0.0031 | 30.28 ± 0.0061 | 57.48 ± 0.0017 |
| Intestinal-Colonic Release | 8.69 ± 0.0044 | 9.78 ± 0.0014 | 19.43 ± 0.0031 |

Compared to the zero-time or day 1 release of NAH-CRG-FU, the gastric release after 2 weeks was more than the zero-time release of the formula by 5.23% and by 1.09% for intestinal-colonic release. After 4 weeks of preparation, the release was increased by more than two folds for the gastric and intestinal phases compared to zero-time release of the formulation. The drug-polymer coating and carrying in the hydrodynamic gel was not highly stable during storage. Initial release of 5-FU right after preparation may influence the shelf-life of the formulation. Also, overall characteristics of NA were affected by aging. NA hydrocolloidal matrix and viscosity needed to capture the free drug were changed with time because of the humidity effect, agitation or microbial infection. Thus, reconstitution of the dry CRG-FU$_k$ powder with the freshly prepared NA solution and CRG$_L$ is preferred rather than storage of the gelling nanosuspension. In general, it is preferred that the nanosuspension be prepared immediately prior to the use to insure the drug release stability.

Evaluation for the volume, weight, strength and durability of the NAH-CRG-FU gel formed in 0.1 M HCl was conducted in comparison to Gaviscon® liquid as a reference (Hampson et al. 2005). For Gaviscon and NAH-CRG-FU formulations, sedimentation volumes after one week of standing in 10 mL cylinders were 0.5 and 0 mL, respectively, reflecting the good physical appearance of the NAH-CRG-FU formulations.

Estimation of Gel Volume and Weight

Glass beakers having a volume of 250 mL were pre-weighed to determine an empty weight (W1) and aliquots of 150 mL HCl were added to each beaker. An aliquot of 15 mL of a formulation was added to the glass beaker. The position of the top of the media level was marked on the outside of the beaker after 30 min of gel formation and the weight (W2) was recorded. The gel was sieved and weighed (W3). The beaker was refilled with water to the marked position and weighed (W4). The gel volume was found using the previously measured weights (gm) as (W4−W1)−(W2−W1−W3). The 1 gm/mL density of the media was assumed.

Gaviscon is a raft-forming liquid formulation with a higher volume and weight than NAH0-CRG-FU nanosuspension formulation by nearly double (Table 6). Gaviscon liquid contains 463.5 mg total solids per 5 mL as a solid content. The NAH-CRG-FU solids content was 360 mg per 5 mL. Additionally, water higher in the Gaviscon in comparison to NAH-CRG-FU nanosuspension. The NA grade utilized in NAH-CRG-FU was a HMWT grade. On other hand, the LMWT grade was the NA grade in Gaviscon. The ability to reach higher NA concentration is provided by the LMWT grade (Hampson et al. 2005 *International Journal of Pharmaceutics*. 294(1):137-147). In Table 6, the formulations showed different gel strengths. These differences are due to the different NA gel cross-linking extents between Gaviscon (least strength) with NA-crosslinking by calcium and NAH-CRG-FU with CRG$_L$ excess gelling (Bani-Jaber and Abdullah 2020 *Pharmaceutical Development and Technology*. 25(6):666-675).

TABLE 6

Gel characterization compared to Gaviscon ®

| Formula | Gel weight (g) ± SD | Gel volume (mL) ± SD | Gel strength (g) ± SD | Gel durability (min) Median | Range |
|---|---|---|---|---|---|
| Gaviscon ® | 53.61 ± 0.014 | 88.60 ± 0.022 | 12.85 ± 0.031 | 38 | 31-41 |
| NAH-CRG-FU | 20.49 ± 0.022 | 30.40 ± 0.015 | 16.50 ± 0.031 | 120 | 120-120 |

Gel Durability in Simulated Gastric Agitation

Aliquots of 15 mL of the suspension were combined with 30 mL of 0.1 M HCl and maintained at 37° C. in 50 mL centrifuge tubes. After 30 min of gel formation, the tube was rotated with 20 rpm using a roller mixer (Roller Mixer-205 RM, Hawashin Tech. Company, Korea). This was to simulate gastric agitation. To a maximum of 120 min or until such time that a gel dissolved, the gel was observed. The gel deterioration time point was recorded as gel durability.

Regarding gel durability, gel of NAH-CRG-FU formulation was more resistant to the agitation than that of Gaviscon® liquid. In Table 6, the median durability time of NAH-CRG-FU gel was nearly 4-fold greater than that of Gaviscon® gel.

Regarding gel durability, gel of NAH-CRG-FU formulation was more resistant to the agitation than that of Gaviscon liquid. In Table 6, the median durability time of NAH-CRG-FU gel was almost 4-fold greater than Gaviscon gel. Resistance against agitation-driven gel deterioration and polymer dissolution was achieved by the use of HMWT-NA. Gel strength and durability are important criteria for performance, since the capture of gastric media inside the gel could decrease the durability of the gel and increase the release of the contents.

Gel Strength

After formation of a gel in 150 mL of 0.1M HCl was maintained at 37° C. in a 250 mL glass beaker, the gel was removed. The gel strength was measured using a Texture Analyzer XT Plus C instrument (Stable Micro Systems, UK) using force output (N=Kg·m/s$^2$). The force was required to rupture the gel by the stainless-steel cone. After dividing the force required by the constant acceleration of the stainless-steel cone, expression of strength in the term of mass (g) was calculated.

Example 4

Physical Characterization of Formulations
Pourability: Residue Test and Angle of Pourability of Nanosuspensions Samples (5 mL) of formulations prepared as in Example 1 were transferred to 25 mL graduated cylinders and gross weights (Wi) were recorded. Each upright cylinder was turned to a flat position over a beaker for 15 second to try to pour the contents into the beaker. After the 15 seconds had elapsed, each beaker was returned to the upright position and a weight (Wf) was recorded. For comparative purposes, the test was repeated on Gaviscon®-liquid as a marketed raft forming preparation. Residue (%) was calculated as ((Wi−Wf)/Wi)*100%. (For the purposes of clarity, these are liquid nanosuspensions, and gelling occurs on contact with acidic media).

For the angle of pourability test, a tablespoon was affixed onto a piece of a carton with an adhesive band and laid on a flat surface with the tablespoon parallel with the floor. In this level position, the affixed spoon was filled with an aliquot of the formulation. As the carton was tilted slowly to the side by hand until the first sign of pouring was observed as dripping, the angle of tilting between the flat surface and the carton carrying the spoon was measured with a protractor as the angle of pourability (θ).

As shown in Table 7, Gaviscon®, as reference product, had slower pourability than NAH-CRG-FU formulation. This was determined by the percent residue after pouring and angle of pourability, both in correlation. One contributing factor to the differences may be due to the fact that Gaviscon contains calcium carbonate. Any solubilization of calcium carbonate by acidic components in the formulation can liberate free calcium that could result in some low degree of NA cross-linking in the formulation vehicle, making the formulation less pourable.

TABLE 7

Pourability test results

| Product | % residue ± SD | Angle of Pourability (θ) ± SD |
|---|---|---|
| Gaviscon ® | 85.42 ± 0.019 | 28.50° ± 0.022 |
| NAH-CRG-FU | 92.59 ± 0.014 | 25.25° ± 0.017 |

Sedimentation Volume 10 mL graduated cylinders were filled with various well-shaken formulations of the NAH-CRG-FU nanosuspension and left to stand for a week at room temperature. At the end of the week, each cylinder was inspected visually to read the volume of the nanosuspension that had sedimented in the cylinder. For Gaviscon® and NAH-CRG-FU formulations, sedimentation volumes after one week of formulation standings in 10 mL cylinders were 0.5 and 0 mL, respectively, reflecting the good physical appearance of the formulations.

Dynamic Viscosity Measurement

A rotational rheometer MCR 301 (Anton Paar/Graz, Austria) was used to measure the dynamic viscosity of the NAH-CRG-FU nanosuspension formulations. A sample volume of 3.8 mL was put in a coaxial cylinder having a gap width 1.128 mm under a temperature of 25±0.01° C. The rate of shear was increased from 2 to 100 sec$^{-1}$, during which shear stress and viscosity were measured for each formulation. The one-point measurement duration was 5 sec. Three measurement intervals were recorded. The flow curve was constructed by a software (Rheoplus®) as shear stress (Pa) versus shear rate (1/s). In addition, the curve of viscosity (Pa·s) versus shear rate (1/s) was plotted.

Figure 8:
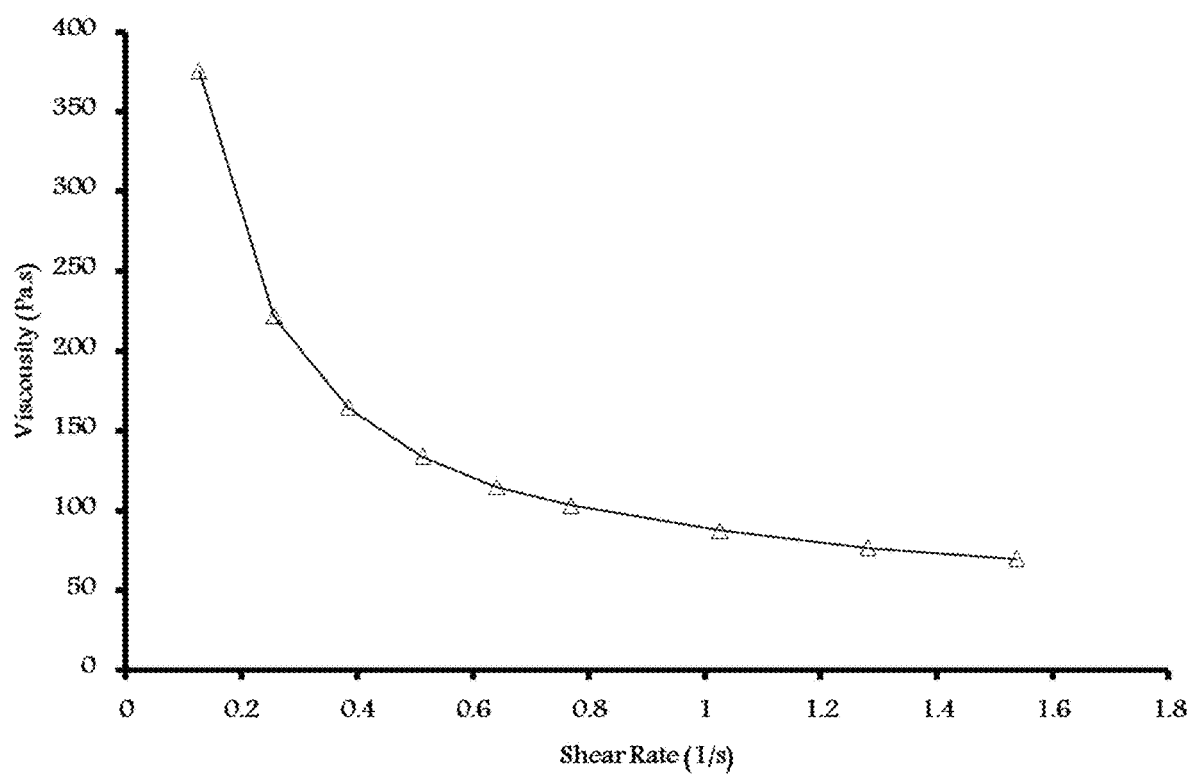
FIG. 8 shows a flow curve of NAH-CRG-FU.
Figure 9:
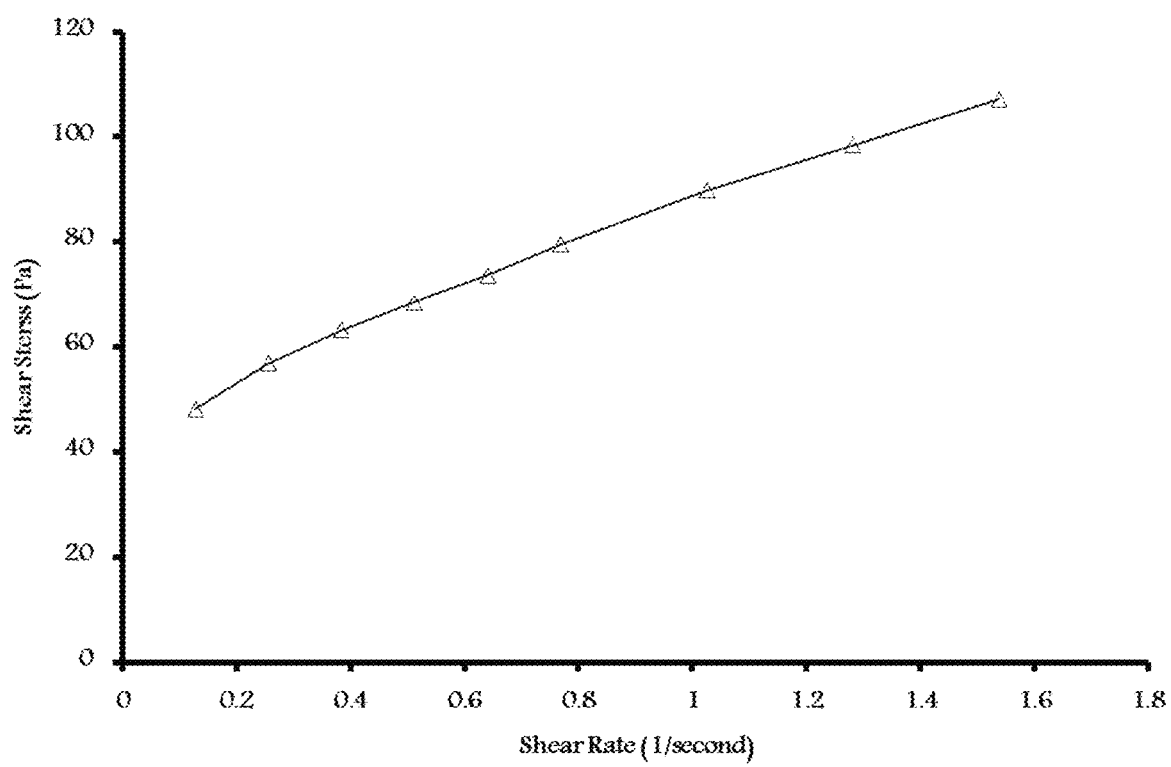
FIG. 9 shows a dynamic viscosity curve of NAH-CRG-FU.

As shown in FIG. 8 and FIG. 9, the viscosity of NAH-CRG-FU formulation sharply and exponentially decreased as a function of shear stress increase. Accordingly, the formulation was non-Newtonian. This is considered pseudo-plastic of shear thinning behavior. This conclusion is further supported by the classification of NA as a hydrocolloid has shear thinning property (Schümmer and Worthoff 1978, Ma et al. 2014). Shear thinning, which occurs considerably at low shear rate, is important for the pourability of the formulations after shaking.

Analysis of Particle Size and Surface Charge of the Suspension

The size distribution, average size and poly-dispersity index of NAH-CRG-FU were obtained by using Zeta-sizer (Malvern Zeta-sizer Nano ZS, from Malvern Instruments Ltd., UK). The 5-fold dilution was made with deionized water to avoid multi-scattering phenomenon. The instrument was coupled with a He—Ne laser lamp (0.4 mW) at wavelength of 633 nm. Measurements were conducted in insulated chamber using dynamic light scattering technique at 25° C. Size measurements were performed using disposable macro-cells. The evaluation of zeta potential was carried out with disposable measurement cells (DTS 1070, Malvern). The measures were made as triplicates. The particle size and distribution, the intensity of each population in size, poly-dispersity index, zeta-potential (ability of aggregation) with surface charge and conductivity of the nanoparticles are all shown in Table 8.

TABLE 8

Analysis of particle size distribution, surface charge and aggregation.

| Product | Average Particle (nm) ± SD | Intensity (%) | Poly dispersity index (PDI) ± SD | Zeta potential (mV) | Conductivity (mS/cm) |
|---|---|---|---|---|---|
| NAH-CRG-FU | 19.62 ± 2.69 | 100% | 0.062 | −40.2 ± 5.38 | 3.05 |

Figure 10:
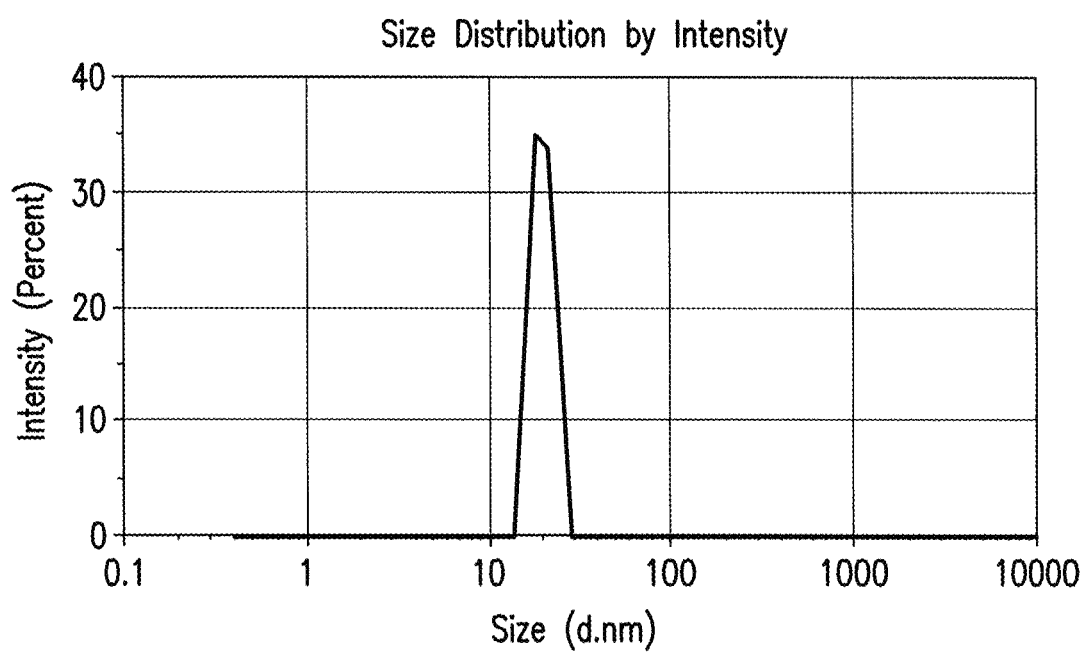
FIG. 10 shows a particle size analysis of NAH-CRG-FU.

The NAH-CRG-FU suspension mean particle size was 15-20 nm, as shown in FIG. 10. The methods of dilution and centrifugation were able to precipitate the large particles and kept the smaller ones in the supernatant layer. It was successful in purifying only the nano-sized particles and excluding the larger particles. The supernatant layer of the diluted and centrifuged formulation sample is considered to be in the nanoparticle range, which is 15-20 nm.

The particle size and distribution are influenced by the shearing force that affected the suspended particles. Thus, the shearing force is an important factor in preparing the (HMWT) NA along with the $CRG_k$ coating on FU. These shearing effects contribute to the characteristics of the formulation. The poly dispersity index (PDI) gives an indication of the ability of the nanoparticles to flocculate or aggregate with time. The PDI value of much less than 1 indicates a low ability for re-aggregation/flocculation but it should be supported with zeta-potential of the particles (Mourdikoudis et al. 2018 *Nanoscale*. 10(27):12871-12934). Zeta-potential values of (±40-±60) mV are considered strong indication of good colloidal nano-particles stability (de-flocculated). This was achieved in the NAH-CRG-FU formulation nanoparticle extract (−40--60) mV. The negative charge was an indication of the presence and dominant vehicle as NA nanoparticle and considered as strong anionic nanoparticles. The conductivity result was consistent with zeta-potential. When the absolute values of the zeta-potential increased, the conductivity increased and this was a validation tool of the method. These results suggested further nanoparticle extract identification, surface identification, morphology of their dispersion and assay of it for the formulation.

Example 5

Analyses of NAH-CRG-FU Nanoparticles

Formulations of NAH-CRG-FU nanoparticles were analyzed to determine particle identity, surface, distribution, morphology and assay of the drug entity. These were identified using particle size analysis, zeta-potential measurements, UV-Vis spectrum and absorbance, FT-IR and scanning electron microscope (SEM) characterizations.

Identification of the Nanoparticles and Drug Content Assay Formulations were analyzed to identify the core of the nanoparticles in the supernatant layer. The supernatant collected by taking 1 mL of the formula and then diluting it up to 5 mL with distilled water. After mixing in a centrifugation tube, the tube was placed in the centrifuge (Thermo Scientific, USA) for 15 minutes under 1500 rpm. The samples were examined using UV-spectrum investigation (Thermo-Scientific, Genesys10S UV-Vis, USA). Additional dilution was sometimes needed to achieve sharp peaks with minimal noise. The sample was checked in triplicates to determine absorbance at 266 nm (5-FU-maximum absorption wavelength).

Figure 11:
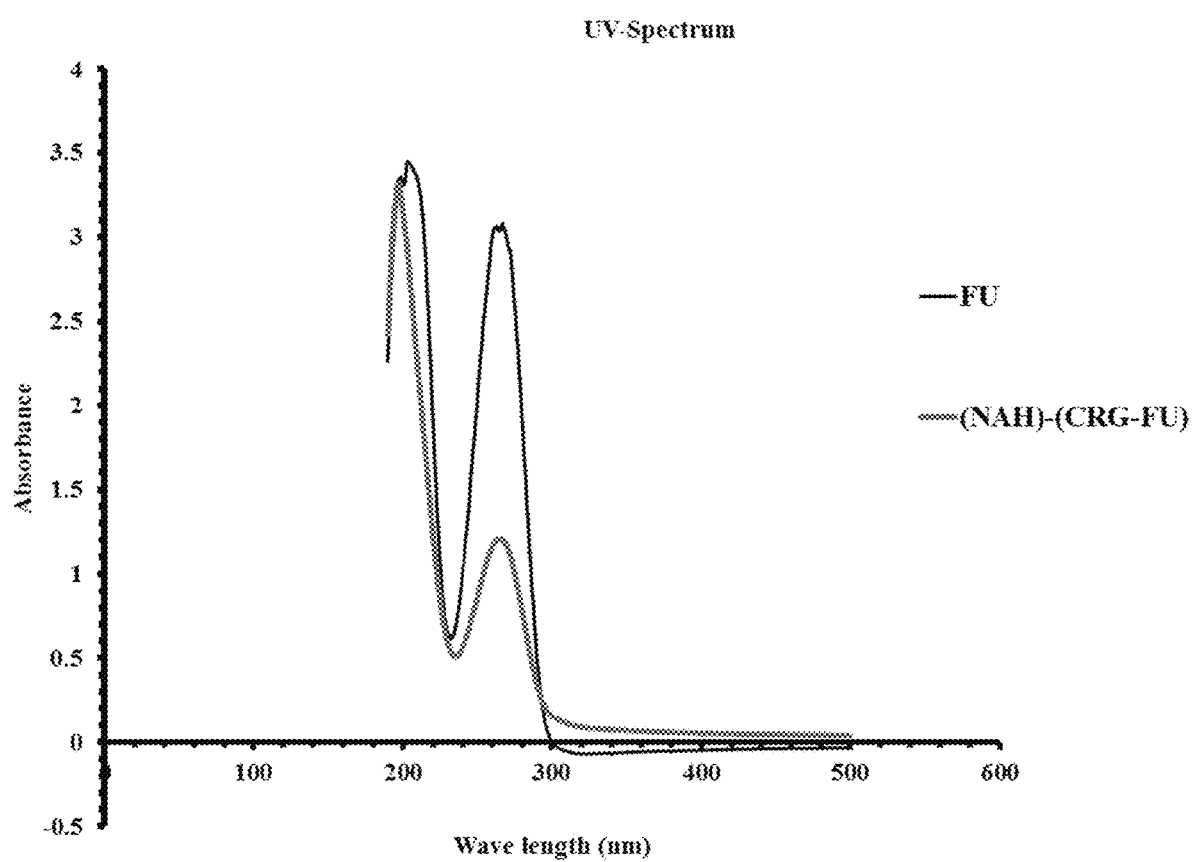
FIG. 11 shows UV-spectra of FU and NAH-CRG-FU.

The spectrum result, shown in FIG. 11, gave spectrum similar to that of the 5-FU spectrum with two distinctive maximum wavelength of absorptions (210 and 266 nm). The formulation supernatant layer showed sharper peaks than the 5-FU. The drug content analysis showed 94.5±0.012% of the total 5-FU in the formulation was extracted in the supernatant layer of NAH-CRG-FU.

Identification of Nanoparticle Surface Character

This test was conducted by direct sampling of liquid supernatant layers of the NAH-CRG-FU nanosuspension after 5-fold dilutions and for NA, CRG-lambda, CRG-kappa and 5-FU using an FTIR spectrophotometer (Thermo-Scientific, Nicolet-iS10, USA). Each sample was compressed using the stainless-steel pin of the instrument. The sample was scanned at laser frequency of 15798.7 cm-1 and medium resolution.

Figure 12:
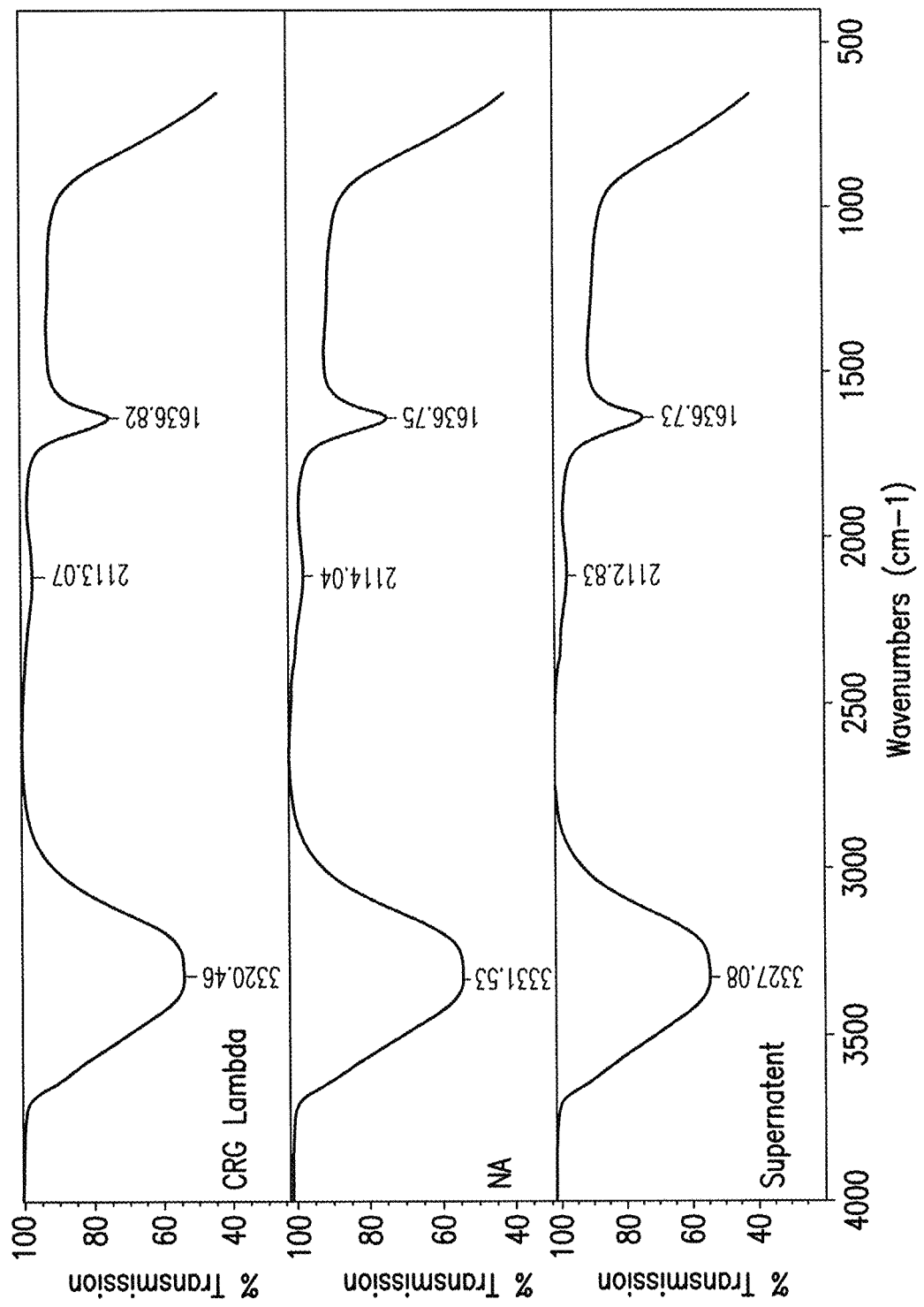
FIG. 12 shows the FTIR spectra of CRG-lambda, NA and NAH-CRG-FU-supernatant layer.

FIG. 12 shows a spectrum for the supernatant layer of NAH-CRG-FU formulation in triplicate. It was highly similar to the NA and CRG-Lambda spectra. This characterization validated the presence the carrier and the coating surfaces around the 5-FU core as in the UV-vis spectroscopy. The NA:CRG ratio was 14.4:1. As a result, the FTIR spectra of the formulation was indicative of the NA coating the core particles and the zeta-potential negative charge confirmed this finding (Mourdikoudis et al. 2018 *Nanoscale*. 10(27): 12871-12934).

Regarding FTIR spectra of NA, the spectrum illustrated the vibration bands of hydroxyl, ether and carboxylic functionalities. Broad peak of (oxygen-hydrogen) bonds displayed in the range of 3000-3600 $cm^{-1}$. Peak of aliphatic (carbon-hydrogen) bond was at 2114.04 $cm^{-1}$. Asymmetric bond vibrations of carboxylate ion at 1636.75 $cm^{-1}$. The (carbon-oxygen) peak of pyranosyl ring, the (carbon-oxygen) stretching and contributions from (carbon-carbon-hydrogen) and (carbon-oxygen-hydrogen) deformations resulted of the band at 935 $cm^{-1}$ (Zhao et al. 2007 *Langmuir*. 23(25):12489-12496). The 5-FU and CRG kappa spectra were included for comparison to FIG. 4A.

Nanoparticle Morphology and Distribution

The morphology and distribution of 5-FU, NA and NAH-CRG-FU supernatant layer were examined by SEM using an electron microscope (FEI Inspect F50, FBI, Tokyo, Japan) and a sputter coater (Emitech K550X, Quorum Technology Ltd., Laughton, UK). The dried specimens were mounted on a metal stub (with double-sided adhesive tape), coated under vacuum with silver and platinum, and scanned at an accelerating voltage of 30 kV.

Figure 13A:
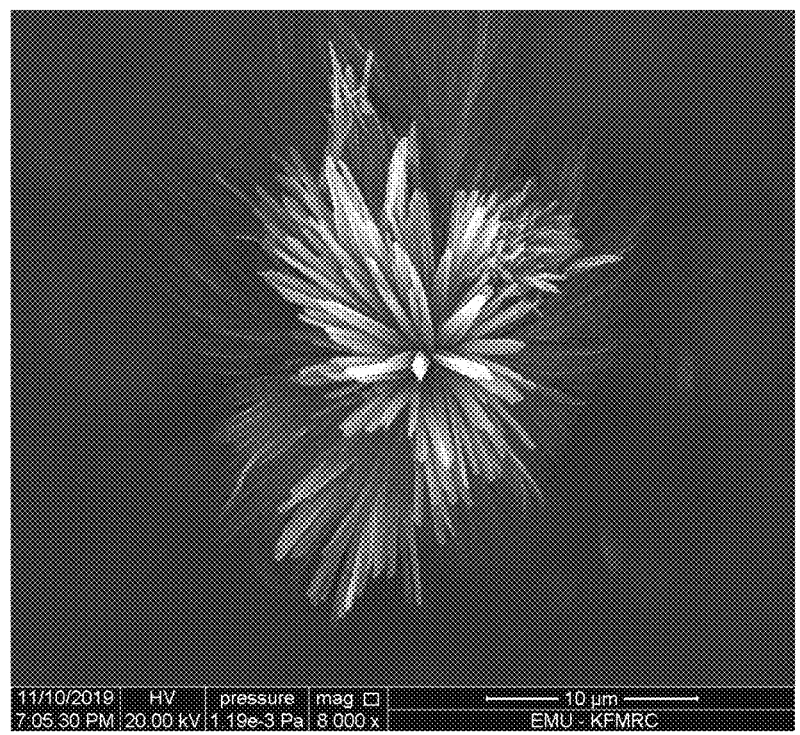
FIGS. 13A-13F show representative images of SEM photomicrographs of (13A) 5-FU, (13B) NA and (13C-13F) NAH-CRG-FU.
Figure 13B:
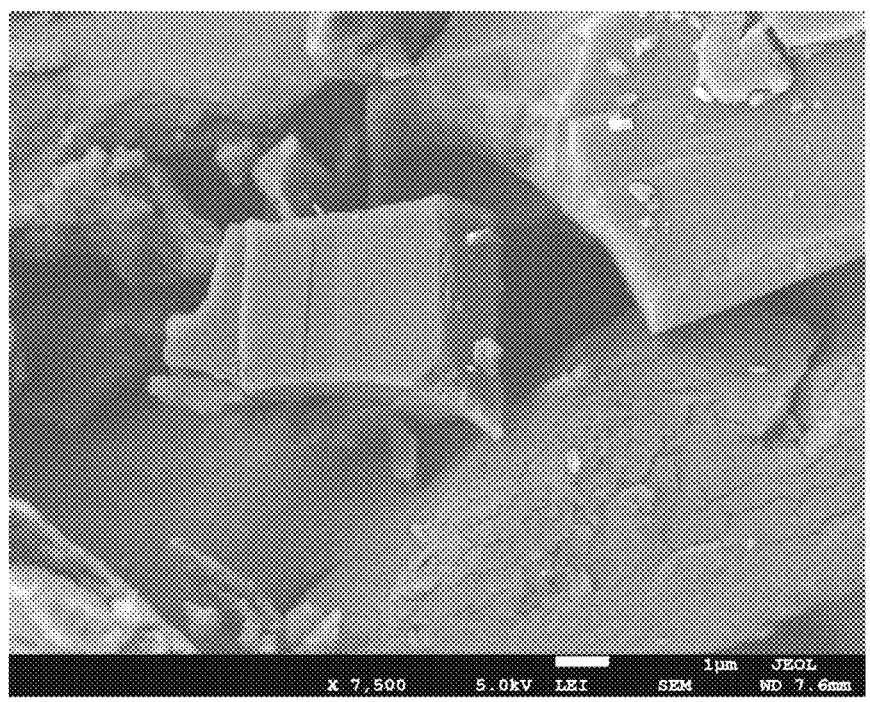
Figure 13C:
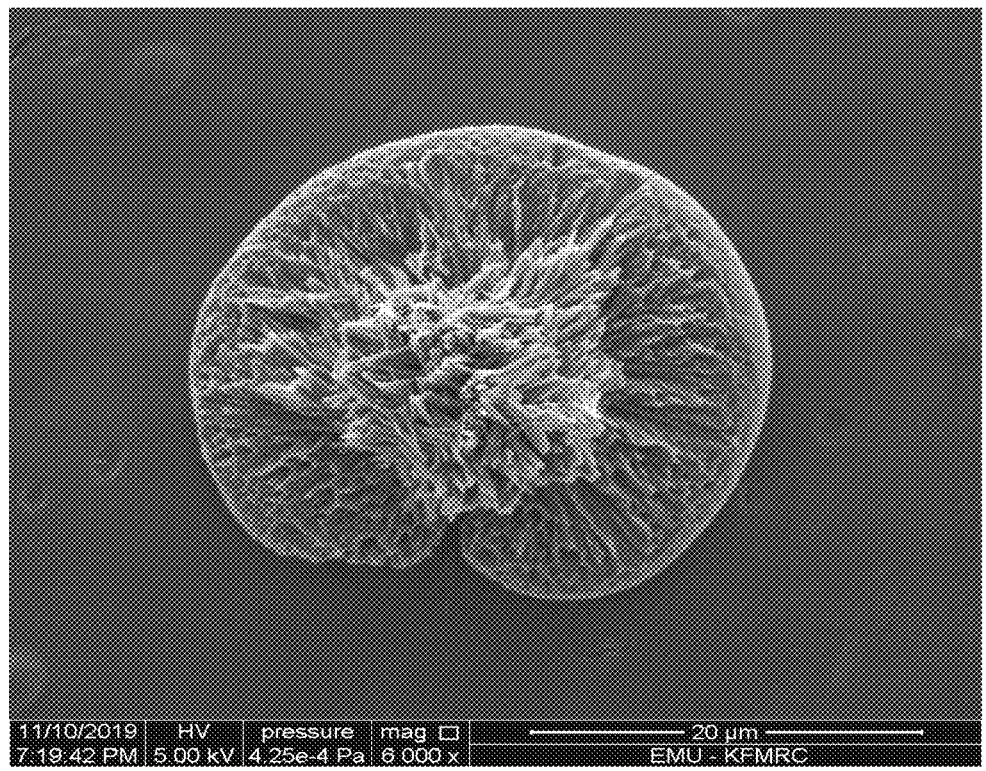
Figure 13D:
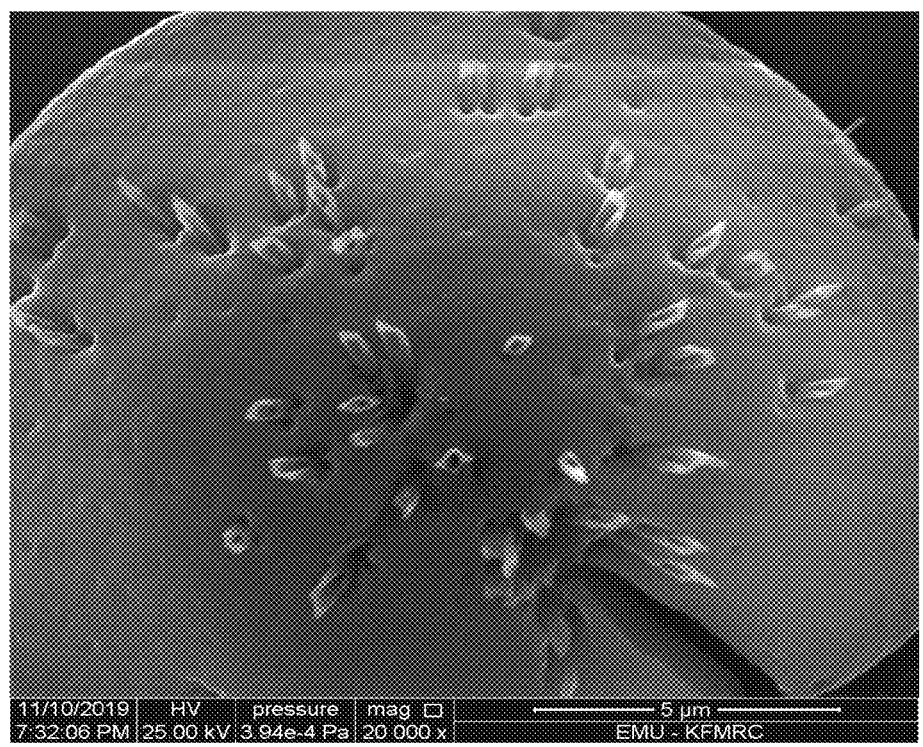
Figure 13E:
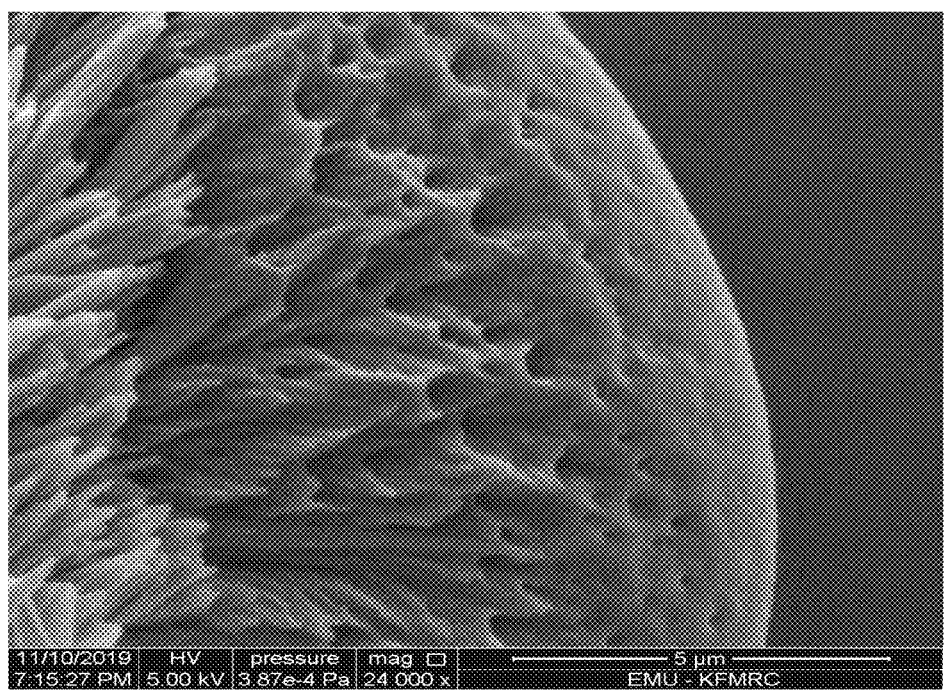
Figure 13F:
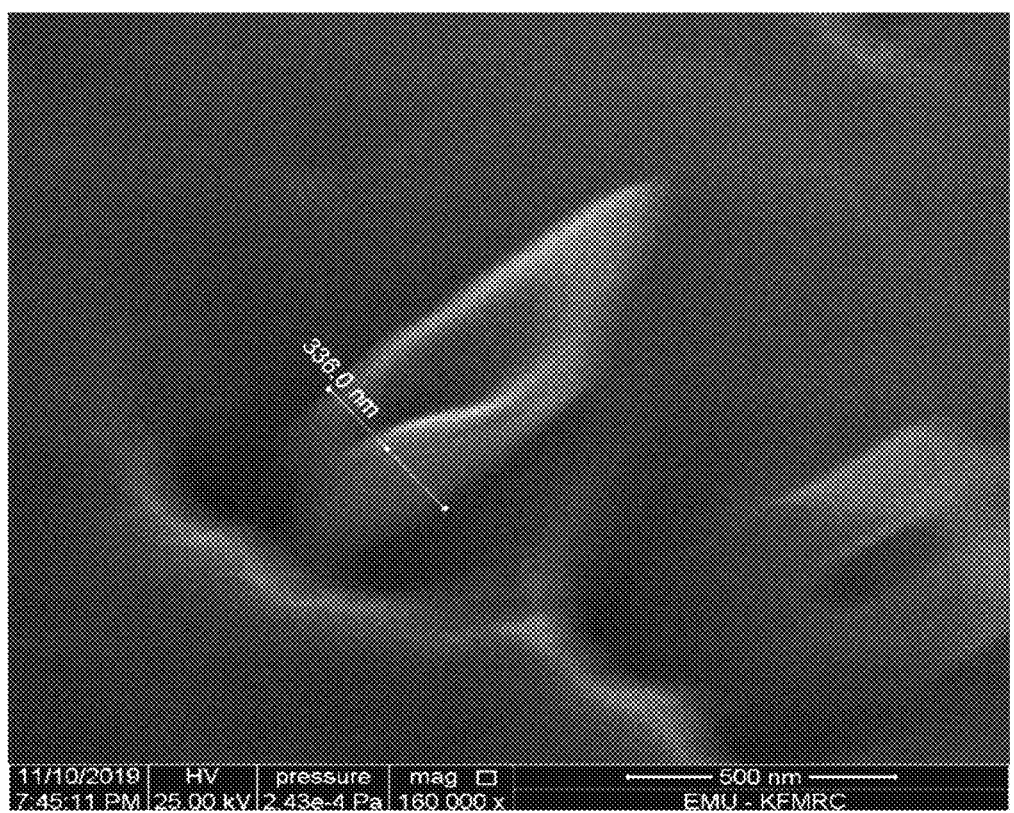

As shown in FIG. 13A, 5-FU crystals have characteristic with regular needle-like structure at a magnification of 8000×. FIG. 13B shows NA powder with a characteristic rectangular shape which might be changed after formulation as the SEM of NAH-CRG-FU supernatant layer suggested. Regarding NAH-CRG-FU, shown in FIGS. 13C-13F, the regular crystalline spikes of 5-FU structures are preserved and appropriately coated with NA and CRG. This explained the PXRD results of the CRG-FU kneaded product and demonstrated that NA preserved this property, as well. The 5-FU needles were extended from the core up to the surfaces of the polymers. The location where the 5-FU needles were free was on the surface of the polymers. These data demonstrate another of the characteristics of the formulation that contribute to increasing the half-life of 5-FU. These results are supported by the particle size analysis, UV-Vis and FT-IR results about the size, the surface charge and identity with the core of the nanoparticles extracted in the supernatant layer.

CONCLUSIONS

Supported by DSC and FT-IR, $CRG_k$ coated the particles of 5-FU to produce crystalline CRG-FU particles as PXRD suggested. The drug-release of the NAH-CRG-FU is characterized by its a sustained-release profile with different rates of release being dependent upon pH. The sustained release of each stage is highly influenced by NA concentration and CRG type coating the 5-FU or contained in the nanosuspension as excess CRG. The $CRG_K$ was used to decrease the 5-FU solubility and availability to cells and metabolic enzymes. Excess $CRG_L$ was used to capture the released 5-FU and strengthen the alginic acid gel. NA was the encapsulating matrix to control and target the release location of the 5-FU release depending on the pH of the gastrointestinal tract. As a result, the formulation was optimized to achieve minimal gastric release with coherence of the insoluble gel, durability and sedimentation in the contact of 0.1N—HCl, followed by slow release performance in the intestinal-colonic area. The sedimentation of the gelling nanosuspension increases the gastric emptying rate and enhances the residency time inside the colonic area as a target site. 5-FU alone gives higher gastric percentage release than NAH-CRG-FU by 31.55% and higher intestinal-colonic percentage release than NAH-CRG-FU by 30.68%. The overall pH-profile release using 5-FU alone is more than NAH-CRG-FU by 62.23%, in contrast to sustained-release of the NAH-CRG-FU gelling nanosuspension that occurs primarily in the favorable pH environment of the colon. The last finding is the original goal that is achieved in this formulation. NAH-CRG-FU aging release study confirmed the need of the re-constitution of the formulation constituents immediately before the administration of the weekly dose. The characterizations of NAH-CRG-FU as nanodrug or a nanosuspension confirmed that the drug would be released in vivo as 5-FU coated nanoparticles with NA. A further benefit of the formulation is the likelihood of inhibiting metabolic conversion before absorption. Additionally, the formulation will protect the gastrointestinal tract from the classic adverse effects of exposure to 5-FU, while the oral bioavailability and safety are enhanced. The high molecular weight and amount of NA are important factors for formation of the gelling nanosuspension and the insoluble gel sedimentation.

While the invention has been described in terms of its several exemplary embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A pharmaceutical composition of 5-fluorouracil (FU) in a gelling nanosuspension, comprising carrageenan-coated FU (CRG-FU) particles with a sodium alginate (NA) coating, wherein the CRG-FU particles with the NA coating are dispersed and suspended in a NA solution, wherein the NA solution becomes an insoluble sedimenting gel at a pH of 3.5 or lower, and wherein the insoluble sedimenting gel reversibly becomes soluble at pH 6 or higher.

2. The pharmaceutical composition of claim 1, wherein CRG-FU is releasable as the insoluble sedimenting gel reversibly becomes soluble.

3. The pharmaceutical composition of claim 2, wherein a rate of dissolution occurs with a mean dissolution time (MDT) according to:

$$MDT = \frac{\sum_{i=1}^{n} t_{mid} \cdot \Delta M}{\sum_{i=1}^{n} \Delta M}$$

wherein i is the number of release samples, n is the number of release times, t is the mid-point time in the interval $(t_{i-1}-t_i)$, and $\Delta M$ is the amount of FU released in the interval $(t_{i-1}-t_i)$.

4. The pharmaceutical composition of claim 1, wherein NA in the NA solution has a molecular weight of 595,000-600,000 g/mole.

5. The pharmaceutical composition of claim 1, wherein the CRG-FU particles have a diameter of 225-250 µm.

6. The pharmaceutical composition of claim 1, wherein the NA coated CRG-FU particles have a diameter of 15 to 20 nm.

7. The pharmaceutical composition of claim 1, wherein the carrageenan is carrageenan-kappa.

8. The pharmaceutical composition of claim 1, wherein the carrageenan is carrageenan-kappa and carrageenan-lambda.

* * * * *